(12) United States Patent
Honma et al.

(10) Patent No.: US 8,049,027 B2
(45) Date of Patent: Nov. 1, 2011

(54) ORGANOSILICON COMPOUND HAVING AMINO GROUP AND ITS PRODUCTION METHOD

(75) Inventors: Takayuki Honma, Joetsu (JP); Tohru Kubota, Joetsu (JP); Ayumu Kiyomori, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 214 days.

(21) Appl. No.: 12/582,026

(22) Filed: Oct. 20, 2009

(65) Prior Publication Data

US 2010/0099866 A1      Apr. 22, 2010

(30) Foreign Application Priority Data

Oct. 22, 2008   (JP) .................................. 2008-271643
Jun. 15, 2009   (JP) .................................. 2009-142152

(51) Int. Cl.
*C07F 7/04*      (2006.01)
*C07F 7/07*      (2006.01)
*C07F 7/08*      (2006.01)

(52) U.S. Cl. .......... 556/423; 556/413; 556/424; 544/69; 544/229

(58) Field of Classification Search ................. None
See application file for complete search history.

(56) References Cited

U.S. PATENT DOCUMENTS

| 5,282,998 A | 2/1994 | Horn et al. |
| 6,841,197 B2 | 1/2005 | Standke et al. |
| 2002/0090316 A1 | 7/2002 | Standke et al. |
| 2006/0161015 A1 | 7/2006 | Klockmann et al. |

FOREIGN PATENT DOCUMENTS

| JP | 2962934 B2 | 10/1999 |
| JP | 2002-226490 A | 8/2002 |
| JP | 2005-2000 A | 1/2005 |
| JP | 2006-249069 A | 9/2006 |

OTHER PUBLICATIONS

European Search Report dated Jan. 14, 2010, issued in corresponding European Patent Application No. 09013164.

*Primary Examiner* — Daniel Sullivan
*Assistant Examiner* — Yevegeny Valenrod
(74) *Attorney, Agent, or Firm* — Westerman, Hattori, Daniels & Adrian, LLP

(57) ABSTRACT

An organosilicon compound having an amino group is provided. This compound is represented by the following general formula (1):

$$R^1\text{-}N(R^2)\text{-}CH\text{-}(O\text{-}SiR^3{}_n(OR^4)_{2-n})\text{-}(CH_2)_3\text{-}O \quad (1)$$

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2. Use of this compound enables production of a polymer product having excellent mechanical properties, high heat resistance, and high transparency. The solution of this compound is stable, and can be stored for a long time, and when used for a polymer modifying agent, it facilitates introduction of amino group and hydroxy group.

13 Claims, 20 Drawing Sheets

ORGANOSILICON COMPOUND HAVING AMINO GROUP AND ITS PRODUCTION METHOD

CROSS-REFERENCE TO RELATED APPLICATION

This non-provisional application claims priority under 35 U.S.C. §119(a) on Patent Application Nos. 2008-271643 and 2009-142152 filed in Japan on Oct. 22, 2008 and Jun. 15, 2009, respectively, the entire contents of which are hereby incorporated by reference.

TECHNICAL FIELD

This invention relates to an organosilicon compound having an amino group which is useful for use as a silane coupling agent, surface treating agent, fiber treating agent, adhesive, additive to a coating composition, or polymer modifier. This invention also relates to its production method.

BACKGROUND ART

An organosilicon compound having an amino group has been known to be useful as a silane coupling agent, surface treating agent, fiber treating agent, adhesive, additive for a coating composition, and the like. More specifically, it has been known that, when an organosilicon compound having an amino group is added to an inorganic material (such as glass fiber, metal, or oxide filler) for the purpose of improving mechanical properties and heat resistance of the polymer material, the effect realized by the addition is enhanced by the improved bond between the polymer material and the inorganic material and improved dispersion of the inorganic material in the polymer material.

In contrast to silicon compounds having an aromatic group such as an aromatic amino group or aniline, the silicon compound having an aliphatic amino group has various merits in addition to the coupling properties as described above such as transparency in the range including UV range, extremely high solubility in water, and capability of use as an aqueous solution which leads to a very wide range of applications by a wide variety of method.

Silane coupling agent including the organosilicon compounds as described above are known to suffer from the problem of generating a considerable amount of alcohol in its use, and in particular, when it is blended in the polymer. Reduction of volatile organic compounds has become an urgent issue in view of global warming and health interests, and efforts have been made to reduce the amount of alcohol generated from the silane coupling agent as a contribution for such reduction of the volatile organic compounds. For example, amount of the alcohol generated in the use of the silane coupling agent is reduced in JP-A 2006-249069 by partly replacing alkoxyl group in the alkoxysilane with an involatile long chain alkyl polyether group, and in Japanese Patent No. 2962934 and JP-A 2002-226490, by producing a siloxane oligomer wherein the alkoxyl group is partly left intact by partly hydrolyzing and condensing the alkoxysilane.

However, production such organosilicon compounds developed for the purpose of reducing the alcohol suffered from various problems in their production, and in particular, when the alcohol is removed by distillation during their production as commonly carried out in producing an organosilicon compound. More specifically, purification by distillation was difficult due to the replacement with the involatile alkoxyl group or increase in the molecular weight due to intermolecular siloxane bond, and this invited decrease in the purity of the yielded product. In the production of such organosilicon compounds, the product was also in the form of a mixture, and this resulted in the insufficient stability of the physical properties. Accordingly, there is a strong demand for the production of an organosilicon compound having an amino group which can be readily purified, and which generates reduced amount of alcohol in its use.

SUMMARY OF THE INVENTION

The present invention has been completed in view of the situation as described above, and an object of the present invention is to provide an organosilicon compound having an aliphatic amino group which can be purified by distillation and which can be produced with reduced amount of alcohol generation. Another object of the present invention is to provide a production method for such organosilicon compound having an aliphatic amino group.

The inventors of the present invention made an intensive study to realize the objects as described above, and found that the organosilicon compound having an amino group represented by the following general formula (1):

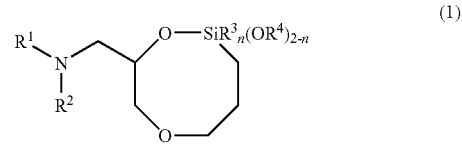

(wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2) can be purified by distillation, and this organosilicon compound enables reduction in the amount of the alcohol generated during its use. It has also been found that the organosilicon compound of the present invention has a very high solubility in the solvent, and can be stored for a long term as a stable alcohol solution or aqueous solution; and that the organosilicon compound of the present invention which is free from active hydrogen atom can be added to a polymer composition having a functional group such as isocyanate group or epoxy group with high reactivity for the active hydrogen without causing any reaction of the functional group so that hydroxy group will be generated by hydrolysis or the like upon its use; and that when used as a terminal modification agent in anionic addition polymerization, the terminal of the anionic polymerization does not react with the oxygen atom in the ring but selectively acts with the alkoxy silicon moiety, and this enables quantitative introduction of the oxygen atom bonded to the silicon atom, and in turn, facilitates production of a polymer modified with amino group and hydroxy group by hydrolysis or the like.

In view of the situation as described above, the present invention provides the organosilicon compound and its production method as described below.

This invention provides an organosilicon compound having an amino group represented by the following general formula (1):

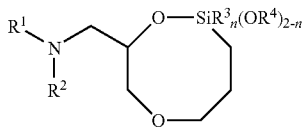

(1)

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2 (claim 1).

This invention also provides a method for producing such an organosilicon compound having an amino group comprising the step of distilling a reaction mixture of an amine compound represented by the following general formula (2):

(2)

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2; with a γ-glycidoxypropylalkoxysilane represented by the following general formula (3):

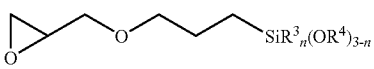

(3)

wherein $R^3$ and $R^4$ are independently an unsubstituted or substituted monovalent hydrocarbon group containing 1 to 10 carbon atoms, and n is an integer of 0 to 2 (claim 2).

In this method, 0.5 to 10 mole of the amine compound of the formula (2) is reacted per mole of the silane compound of the formula (3), and the reaction is conducted at a temperature of 50 to 200° C. (claim 3).

This invention also provides a compound produced by such method wherein a compound is a mixture of the compound represented by the following general formula (1), a compound represented by the following general formula (4), a compound represented by the following general formula (5), and a compound represented by the following general formula (6):

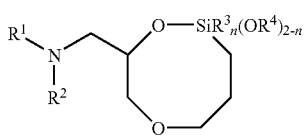

(1)

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; n represents an integer of 0 to 2, and m is 0 or 1, with the proviso that m is 0 when n is 0, and m is 1 when n is 1, and compound of the general formula (6) is absent when n is 2 at a weight ratio of 1 to 80%:1 to 70%:1 to 40%:0 to 20% (claim 5).

This invention also provides a method for producing the organosilicon compound having an amino group comprising the steps of reacting an amine compound represented by the following general formula (2):

(2)

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; with a γ-glycidoxypropyl alkoxysilane represented by the following general formula (3):

(3)

wherein $R^3$ and $R^4$ independently represents an unsubstituted or substituted monovalent hydrocarbon group containing 1 to 10 carbon atoms and n is an integer of 0 to 2; wherein the reaction is conducted while distilling off alcohol generated in the reaction (claim 5).

In this method, a solvent having a boiling point higher than the alcohol generated in the reaction may be used, and when the solvent is used, the reaction is conducted by refluxing the solvent (claim 6).

In this method, the amine compound represented by the general formula (2) is heated in a distillation tank to a temperature higher than its boiling point for evaporation, and the evaporated amine compound is added to a distillation column from its lower end, while supplying the γ-glycidoxypropyla-lkoxysilane represented by the general formula (3) to the distillation column from its upper end; and the reaction is conducted while the alcohol generated in the reaction is distilled off from the upper end of the distillation column (claim 7).

In this method, the reaction may be conducted in the presence of a basic catalyst (claim 8).

This method may further comprise a step in which the reaction mixture produced by any one of the method as described above is distilled in the presence of a basic compound (claim 9).

In any of the method as described above, the basic compound may be an inorganic base (claim 10), and the basic catalyst may be an inorganic base (claim 11), and the inorganic base may be an alkali metal alkoxide (claim 12).

This invention also provides a mixture produced by the method as described above wherein a compound represented by the following general formula (1), a compound represented by the following general formula (4), a compound represented by the following general formula (5), a compound represented by the following general formula (6):

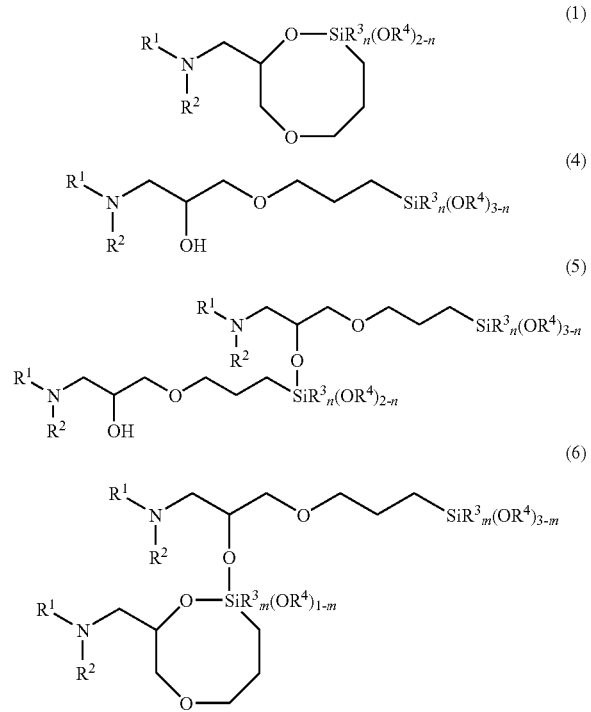

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; n represents an integer of 0 to 2, and m is 0 or 1, with the proviso that m is 0 when n is 0, and m is 1 when n is 1, and compound of the general formula (6) is absent when n is 2 are mixed at a weight ratio of 1 to 90%:0 to 30%:0 to 30%:1 to 60% (claim 13).

Advantageous Effects of Invention

Use of the organosilicon compound having an amino group of the present invention enables production of a polymer product having excellent mechanical properties as well as high heat resistance with transparency of the polymer material retained in the range including UV range. The solution of the organosilicon compound of the present invention can be stored for a long time due to its high stability, and when used for a polymer modifying agent, it facilitates introduction of amino group and hydroxy group in the polymer. The present invention has also realized simple production at high yield of an organosilicon compound which allows easy purification and which generates reduced amount of alcohol during the use.

DETAILED DESCRIPTION OF THE INVENTION

Figure 1:
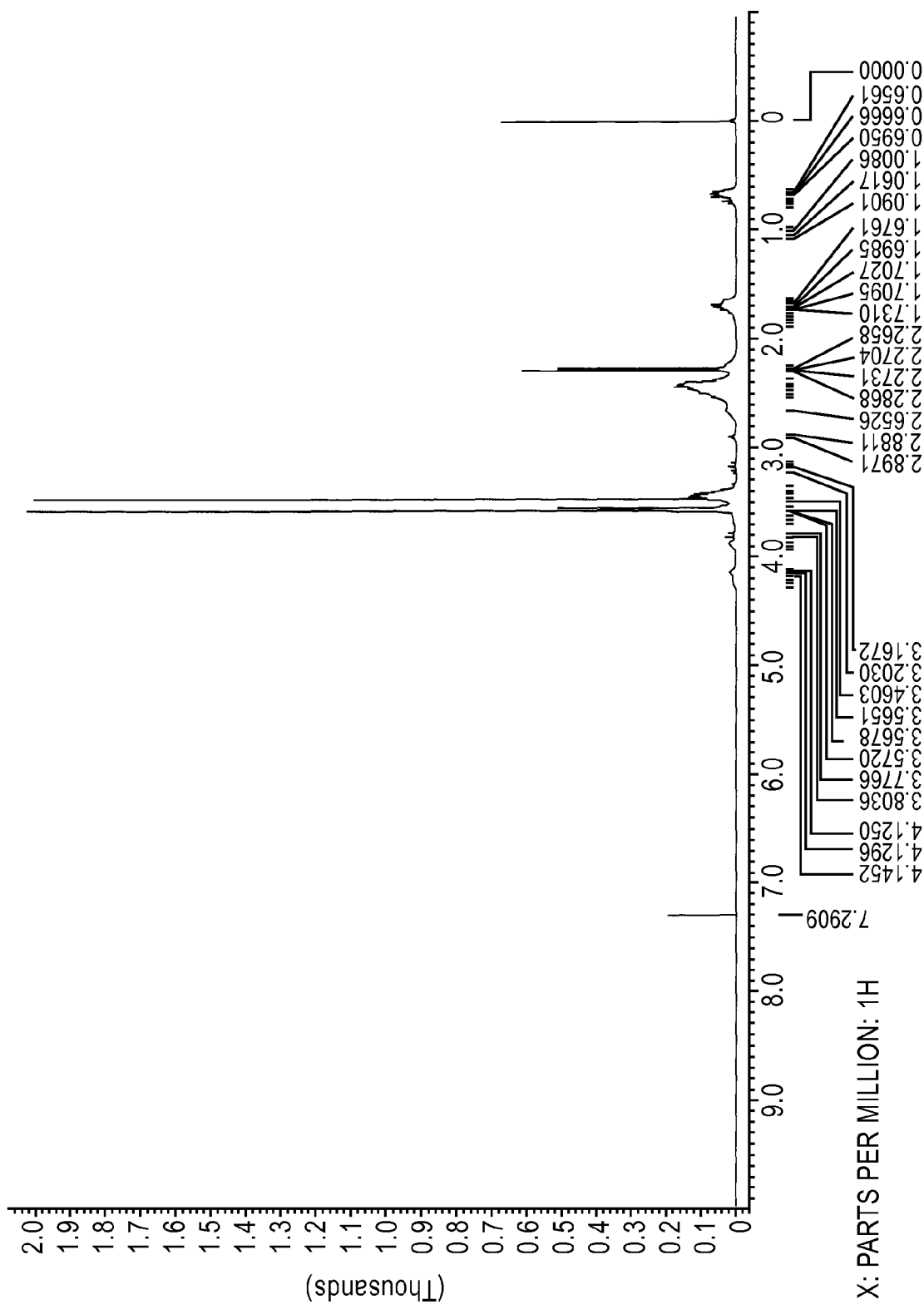
FIG. 1 is the $^1$H-NMR spectrum of the composition produced in Synthetic Example 1.

The organosilicon compound having an amino group of the present invention is an organosilicon compound having an amino group represented by the following general formula (1):

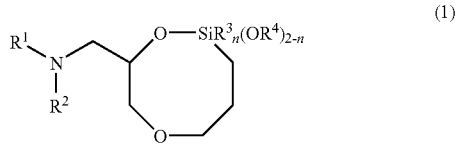

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2. This organosilicon compound having an amino group is produced by distilling a reaction mixture of an amine compound represented by the following general formula (2):

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2; with a γ-glycidoxypropylalkoxysilane represented by the following general formula (3):

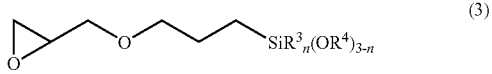

wherein $R^3$ and $R^4$ are independently an unsubstituted or substituted monovalent hydrocarbon group containing 1 to 10 carbon atoms, and n is an integer of 0 to 2.

In the general formulae (1) and (2), $R^1$ and $R^2$ are independently an unsubstituted or substituted aliphatic monovalent hydrocarbon group containing 1 to 10 carbon atoms, and $R^1$ and $R^2$ may also together form a ring with the nitrogen atom to which they are bonded to. $R^1$ and $R^2$ may also contain a heteroatom. Examples include aliphatic monovalent hydrocarbon groups such as straight chain, branched, or cyclic alkyl groups, for example, methyl group, ethyl group, n-propyl group, isopropyl group, n-butyl group, isobutyl group, tert-butyl group, sec-butyl group, n-pentyl group, isopentyl group, neopentyl group, cyclopentyl group, n-hexyl group, isohexyl group, cyclohexyl group, n-heptyl group, isoheptyl group, n-octyl group, isooctyl group, tert-octyl group, n-nonyl group, isononyl group, n-decyl group, isodecyl group, n-undecyl group, isoundecyl group, n-dodecyl group, and isododecyl group. When $R^1$ and $R^2$ together form a ring, the $R^1R^2N$— will be a nitrogen-containing heterocyclic group, and this nitrogen-containing heterocyclic group may be unsubstituted or substituted with a substituent. Exemplary substituents include alkyl groups such as methyl group, ethyl group, (iso)propyl group, and hexyl group; alkoxy groups such as methoxy group, ethoxy group, and (iso)propoxy group; groups comprising a halogen atom such as fluorine atom, chlorine atom, bromine atom, and iodine atom; cyano group, amino group, aromatic hydrocarbon group, ester group, ether group, acyl group, and thioether group, which may be used in combination of two or more. These substituents are not limited for their position of the substitution and for their number. Examples of such nitrogen-containing heterocyclic group include piperidine, piperazine, morpholine, pyrrolidine, pyrrolidone, piperidone, and their derivatives.

Examples of the compound represented by the general formula (2) are given below. In the following formulae, Me stands for methyl group, Et stands for ethyl group, Pr stands for propyl group, Bu stands for butyl group, and c-$C_6H_{11}$ stands for cyclohexyl group.

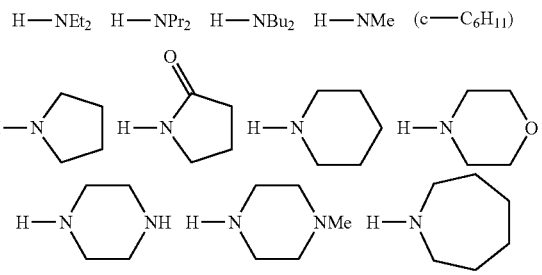

In formulae (1) and (3), $R^3$ and $R^4$ are a monovalent hydrocarbon group containing 1 to 10, and preferably 1 to 6 carbon atoms, and exemplary such groups include straight chain, branched, and cyclic alkyl groups, alkenyl groups, and aryl groups, for example, methyl group, ethyl group, propyl group, isopropyl group, butyl group, isobutyl group, tert-butyl group, pentyl group, cyclopentyl group, hexyl group, cyclohexyl group, heptyl group, octyl group, decyl group, vinyl group, allyl group, methallyl group, and butenyl group.

Examples of the compound represented by the general formula (3) include γ-glycidoxypropyltrimethoxysilane, γ-glycidoxypropylmethyldimethoxysilane, γ-glycidoxypropyldimethylmethoxysilane, γ-glycidoxypropyltriethoxysilane, γ-glycidoxypropylmethyl diethoxysilane, and γ-glycidoxypropyldimethylethoxysilane.

Examples of the compound represented by the general formula (1) include 1,1-dimethoxy-3-N,N-diethylaminomethyl-2,5-dioxa-1-silacyclooctane, 1,1-dimethoxy-3-piperidinomethyl-2,5-dioxa-1-silacyclooctane, 1,1-dimethoxy-3-morpholinomethyl-2,5-dioxa-1-silacyclooctane, 1,1-dimethoxy-3-piperadinomethyl-2,5-dioxa-1-silacyclooctane, 1,1-dimethoxy-3-(4-methylpiperidino)methyl-2,5-dioxa-1-silacyclooctane, 1,1-dimethoxy-3-hexamethyleneiminomethyl-2,5-dioxa-1-silacyclooctane, 1,1-diethoxy-3-N,N-diethylaminomethyl-2,5-dioxa-1-silacyclooctane, 1,1-diethoxy-3-piperidinomethyl-2,5-dioxa-1-silacyclooctane, 1,1-diethoxy-3-morpholinomethyl-2,5-dioxa-1-silacyclooctane, 1,1-diethoxy-3-piperadinomethyl-2,5-dioxa-1-silacyclooctane, 1,1-diethoxy-3-(4-methylpiperadino)methyl-2,5-dioxa-1-silacyclooctane, 1,1-diethoxy-3-hexamethyleneiminomethyl-2,5-dioxa-1-silacyclooctane, 1-methoxy-1-methyl-3-N,N-diethylaminomethyl-2,5-dioxa-1-silacyclooctane, 1-methoxy-1-methyl-3-piperidinomethyl-2,5-dioxa-1-silacyclooctane, 1-methoxy-1-methyl-3-morpholinomethyl-2,5- dioxa-1-silacyclooctane, 1-methoxy-1-methyl-3-piperadinomethyl-2,5-dioxa-1-silacyclooctane, 1-methoxy-1-methyl-3-(4-methylpiperadino)methyl-2,5-dioxa-1-silacyclooctane, 1-methoxy-1-methyl-3-hexamethyleneiminomethyl-2,5-dioxa-1-silacyclooctane, 1-ethoxy-1-methyl-3-N,N-diethylaminomethyl-2,5-dioxa-1-silacyclooctane, 1-ethoxy-1-methyl-3-piperidinomethyl-2,5-dioxa-1-silacyclooctane, 1-ethoxy-1-methyl-3-morpholinomethyl-2,5-dioxa-1-silacyclooctane, 1-ethoxy-1-methyl-3-piperadinomethyl-2,5-dioxa-1-silacyclooctane, 1-ethoxy-1-methyl-3-(4-methylpiperadino)methyl-2,5-dioxa-1-silacyclooctane, and 1-ethoxy-1-methyl-3-hexamethyleneiminomethyl-2,5-dioxa-1-silacyclooctane.

In reacting the amine compound of the general formula (2) with the γ-glycidoxypropylalkoxysilane compound of the general formula (3), ratio of the amine compound of the general formula (2) to the γ-glycidoxypropylalkoxysilane compound of the general formula (3) is not particularly limited. The amine compound of the general formula (2), however, is typically used at 0.5 to 10 mole, preferably at 0.5 to 5 mole, more preferably at 0.8 to 5 mole per mole of the silane compound represented by the general formula (3).

The reaction temperature of this reaction is not particularly limited. However, the reaction is typically conducted at 50 to 200° C., preferably at 70 to 200° C., and more preferably at 80 to 160° C. for a reaction time of preferably 1 to 20 hours, and more preferably 1 to 15 hours.

This reaction can proceed without any solvent. However, the reaction can be promoted in the presence of a solvent. Exemplary solvents which may be used in this reaction include hydrocarbon solvents such as pentane, hexane, cyclohexane, heptane, isooctane, benzene, toluene, and xylene, alcohol solvents such as methanol and ethanol, ether solvents such as diethylether, tetrahydrofuran, and dioxane, ester solvents such as ethyl acetate and butyl acetate, aprotic polar solvents such as acetonitrile and N,N-dimethylformamide, and chlorinated hydrocarbon solvents such as dichloromethane and chloroform, which may be used alone or in combination of two or more.

The reaction of the amine compound of the general formula (2) with the γ-glycidoxypropylalkoxysilane compound of the general formula (3) yields a reaction mixture, and the organosilicon compound represented by the general formula (1) can be readily isolated from this reaction mixture by distillation or other purification procedure such as column separation, and the preferred is the use of distillation in view of the high purity of the resulting product. The conditions used for the distillation is not particularly limited. However, the distillation is preferably carried out under reduced pressure for reducing the boiling point.

The reaction mixture obtained is a mixed composition of an organosilicon compound represented by the following general formula (4):

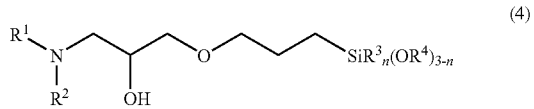

wherein $R^1$, $R^2$, $R^3$, $R^4$ and n are as defined above for the general formula (1); its dealcoholized condensate represented by the following general formula (1)

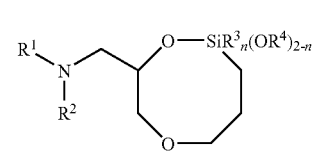

wherein $R^1$, $R^2$, $R^3$, $R^4$ and n are as defined above; an organosilicon compound represented by the following general formula (5):

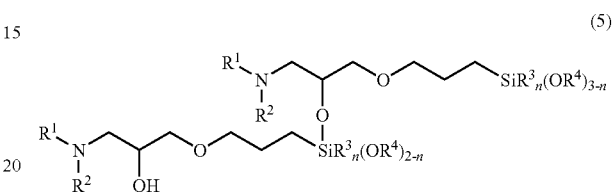

wherein $R^1$, $R^2$, $R^3$, $R^4$ and n are as defined above for the general formula (1); and a compound represented by the following general formula (6):

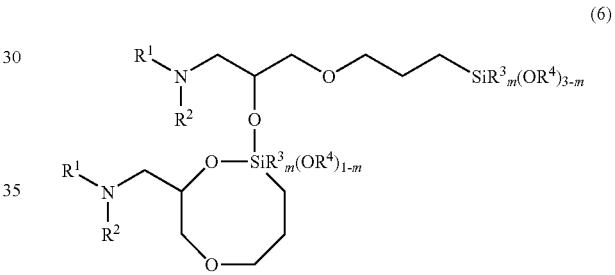

wherein $R^1$, $R^2$, $R^3$ and $R^4$ are as defined above for the general formula (1), and m is 0 or 1.

$R^1$, $R^2$, $R^3$, $R^4$, and n in the condensates represented by the general formulae (1) and (4) to (6) are as defined above.

More specifically, $R^3$ and $R^4$ in the condensates represented by the general formulae (1) and (4) to (6) are preferably methyl group or ethyl group, and m is 0 when n is 0, m is 1 when n is 1, and both the compound of the general formula (6) and m are absent when n is 2.

The weight ratio of the compound constituting the reaction mixture produced by the method as described above is not particularly limited. The weight ratio of the compound of the general formula (1):the compound of the general formula (4):the compound of the general formula (5):the compound of the general formula (6), however, is preferably in the range of (1 to 80):(1 to 70):(1 to 40):(0 to 20), and more preferably in the range of (30 to 80):(30 to 70):(1 to 20):(0 to 10).

In the preferable embodiment of the method of the present invention, the γ-glycidoxypropylalkoxysilane compound of the general formula (3) is added to the amine compound of the formula (2), and during this reaction, the alcohol generated is removed by distillation. In this case, the organosilicon compound of the formula (1) of the present invention is generated by dealcoholization of the compound of the following formula (4):

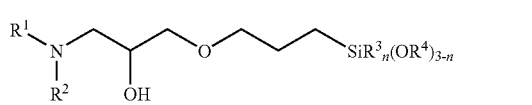

(4)

wherein $R^1$ to $R^4$, and n are as defined above formed from the amine compound of the general formula (2) and the alkoxysilane of the formula (3).

In this production method, ratio of the amine compound represented by the general formula (2) to the γ-glycidoxypropylalkoxysilane compound represented by the general formula (3) is not particularly limited. However, the amine compound represented by the general formula (2) is preferably used at an amount in the range of 0.8 to 10 mole, and more preferably at 1.0 to 5.0 mole per mole of the γ-glycidoxypropylalkoxysilane compound represented by the general formula (3) in view of the reactivity and the productivity.

The reaction temperature for the reaction is also not particularly limited. The reaction, however, is preferably conducted at 50 to 200° C., and more preferably at 80 to 160° C. for a reaction time of 1 to 20 hours, and more preferably, for 1 to 15 hours.

The pressure during the reaction is not particularly limited. However, the reaction is preferably conducted at normal or reduced pressure in order to facilitate the distillation of the generated alcohol.

The reaction can proceed either without or with the solvent. When proceeded with a solvent, the solvent used may be the same as the one as described above. The solvent, however, is preferably the one having a boiling point higher than that of the alcohol generated in the reaction for ease of the distillation of the generated alcohol. The reaction is preferably conducted by refluxing the solvent.

When the solvent is the amine compound itself, the distillation column is used and the amine compound heated in the distillation tank is fed from the lower end of the distillation column while the γ-glycidoxypropylalkoxysilane represented by the general formula (3) is fed from the upper end of the distillation column to allow the reaction between the amine compound and the alkoxysilane represented by the general formula (3) to proceed in the distillation column, and in the meanwhile, the alcohol generated in the reaction is preferably removed from the upper end of the distillation column by distillation so that the condensation between the molecules of the compound represented by the general formula (4) generated by ring opening addition reaction between the amino group and the epoxy group will be reduced, and the target compound represented by the general formula (1) will be produced at a higher yield. This is because, when two reactions, namely, the ring opening addition reaction and the dealcoholization reaction are completed in the distillation column, the compound represented by the general formula (4) will present in the distillation column at a lower concentration, and the intramolecular reaction will be promoted simultaneously with the dealcoholization, while, if the reactions are not completed in the column, the compound represented by the general formula (4) will present in the distillation column at a high concentration and intermolecular condensation will be promoted during the dealcoholization. Accordingly, when the reaction is conducted in a distillation column, the yield can be improved by allowing the reaction to be completed in the distillation column, and therefore, it is important to select a reaction time, namely, a residence time in the distillation column adequate for the reaction speed.

The distillation column is not particularly limited for its structure, and the distillation column commonly used for the distillation can be used. Height of the distillation column can be determined from economical point of view. The packing material filled in the distillation column is not particularly limited for its type and structure, and exemplary packing materials include Raschig ring, Lessing ring, Pall ring, saddle, helix, and Sulzer packing, and the distillation column may have a structure including, for example, a porous plate or a wetted wall. Since the reaction speed depends on the structure and the basicity of the amine and the alkoxysilane, a packing material and structure facilitating longer residence time in the column, namely larger number of theoretical plates in the distillation column is preferable when the amine or the alkoxysilane with low reactivity is used.

The alcohol generated in the reaction is preferably distilled off the reaction vessel as a gas or condensed liquid. The alcohol is preferably distilled off together with the solvent used in the reaction since the alcohol can be removed at a higher efficiency. Amount of the solvent used in the reaction can be reduced if the solvent is separated form the removed fraction and recycled into the reaction vessel.

This reaction can be promoted without using any catalyst. However, when a catalyst used, the catalyst may be the catalyst commonly used in the transesterification including acidic, basic, and transition metal catalysts. The preferred is the basic catalyst. Exemplary basic catalysts are alkali metal hydroxides, alkaline earth metal hydroxides, alkali metal alkoxides, alkaline earth metal alkoxides, and quaternary ammonium hydroxides including alkali metal hydroxides such as potassium hydroxide, sodium hydroxide, and cesium hydroxide; alkali metal alkoxides such as potassium methoxide, sodium methoxide, potassium ethoxide, and sodium ethoxide; and quaternary ammonium hydroxide having an alkyl or aryl group such as tetramethylammonium hydroxide, tetraethylammonium hydroxide, tetrapropylammonium hydroxide, tetrabutylammonium hydroxide, and trimethylbenzylammonium hydroxide; and the most preferred are alkali metal alkoxides. The basic catalyst may be used as an aqueous solution or alcohol solution.

The catalyst as described above may be used either alone or in combination of two or more, and the ratio of the catalyst is not particularly limited. The catalyst, however, is preferably used at a ratio of 0.001 to 1.0 mole, and more preferably, at 0.005 to 0.1 mole per mole of the silicon atom. When the catalyst used is insufficient, the effects of the catalyst addition may also be insufficient while addition of excessive catalyst may not necessary result in the reaction promotion effect that corresponds to the amount added.

The organosilicon compound represented by the general formula (1) may also be isolated from the reaction composition by purification such as distillation and column separation, and the isolation by distillation is preferable in view of the simplicity and high purity of the isolated product. The condition used for the distillation is not particularly limited. The distillation, however, is preferably conducted at a reduced pressure to thereby reduce the boiling point.

Although no additive is required in the distillation, the distillation can be accomplished by using a basic compound. Examples of such basic compound include alkali metal hydroxides, alkali metal alkoxides, and quaternary ammonium hydroxides. More specifically, the basic compound may be an alkali metal hydroxide such as potassium hydroxide, sodium hydroxide, or cesium hydroxide; an alkali metal alkoxide such as potassium methoxide, sodium methoxide, potassium ethoxide, and sodium ethoxide; a quaternary ammonium hydroxide having an alkyl or aryl group such as tetramethylammonium hydroxide, tetraethylammonium hydroxide, tetrapropylammonium hydroxide, tetrabutylammonium hydroxidllle, and trimethylbenzylammonium hydroxide; and the most preferred are alkali metal alkoxides. The basic compound may be used as an aqueous solution or an alcohol solution.

The basic compound may be used at a ratio of preferably 0.001 to 1.0 mole, and more preferably 0.005 to 0.1 mole per mole of the silicon atom. When the basic compound is used at an insufficient amount, the effects of the addition may also be insufficient while addition of excessive basic compound may not necessary result in the reaction promotion effect that corresponds to the amount added. The basic compound added during the reaction may be used as the basic compound in the distillation.

The organosilicon compound of the present invention can be used with no further processing. The organosilicon compound, however, is preferably diluted in a solvent before its use for the convenience of the handling. Exemplary solvents used for such purpose include water; alcohol solvents such as methanol and ethanol; hydrocarbon solvents such as hexane, cyclohexane, heptane, isooctane, benzene, toluene, and xylene; ketene solvents such as acetone and methyl isobutyl ketene; ether solvents such as diethylether, tetrahydrofuran, and dioxane; ester solvents such as ethyl acetate and butyl acetate; aprotic polar solvents such as acetonitrile and N,N-dimethylformamide; and chlorinated hydrocarbon solvents such as dichloromethane and chloroform. Particularly preferred are water and alcohol solvents. The solvent may be used so that the organosilicon compound is diluted to a concentration of 0.001 to 50% by weight.

The weight ratio of the compound in the reaction mixture produced by the method as described above is not particularly limited. The weight ratio of the compound of the general formula (1):the compound of the general formula (4):the compound of the general formula (5):the compound of the general formula (6), however, is preferably in the range of (1 to 90):(0 to 30):(0 to 30):(1 to 60), and more preferably (30 to 90):(0 to 20):(0 to 20):(1 to 40).

The organosilicon compound of the present invention may contain at least one additive selected from pigment, antifoaming agent, lubricant, antiseptic agent, pH adjusting agent, film forming agent, antistatic agent, antimicrobial agent, surfactant, dye, and the like to the extent not adversely affecting the merit of the present invention.

The organosilicon compound of the present invention can be used for unlimited range of applications, for example, surface treatment of an inorganic filler, liquid potting agent, cast molding, surface modification of a resin surface, polymer modifier, and additive of an aqueous coating composition.

An inorganic filler can be surface treated with the organosilicon compound of the present invention. Examples of the inorganic filler include glass fiber, powder silica, powder alumina, powder talc, and powder calcium carbonate, and the glass fiber may be prepared by using the type of the glass commonly used in the art such as E glass and C glass. The glass fiber is not limited for its shape, and a wide variety of glass fiber products may be used as a bundle of glass yarns (filaments) each having a fiber diameter of 3 to 30 μm, a thrown yarn, and woven product.

The method used for treating the inorganic filler with the organosilicon compound may be a method commonly used in the art. More specifically, the surface treating agent of the present invention can be used either with or without dilution, and the inorganic filler may be immersed in the surface treating agent, removed from the surface treating agent, and dried. Alternatively, the diluted or non-diluted surface treating agent may be sprayed to the surface of the inorganic filler, followed by drying.

EXAMPLES

Next, the present invention is described in further detail by referring to Synthetic Examples and Examples of the invention which by no means limit the scope of the present invention. In the following description, Me stands for methyl group and Et stands for ethyl group.

Synthetic Example 1

Reaction of methylpiperazine with γ-glycidoxypropyl-trimethoxysilan

A flask equipped with a stirrer, a reflux condenser, a dropping funnel, and a thermometer was charged with 30 g (0.30 mole) of methylpiperazine, and 71 g (0.30 mole) of γ-glycidoxypropyltrimethoxysilane was added dropwise at 85 to 95° C. for 4 hours, and the mixture was stirred at the same temperature for 2 hours to obtain a transparent composition.

Figure 2:
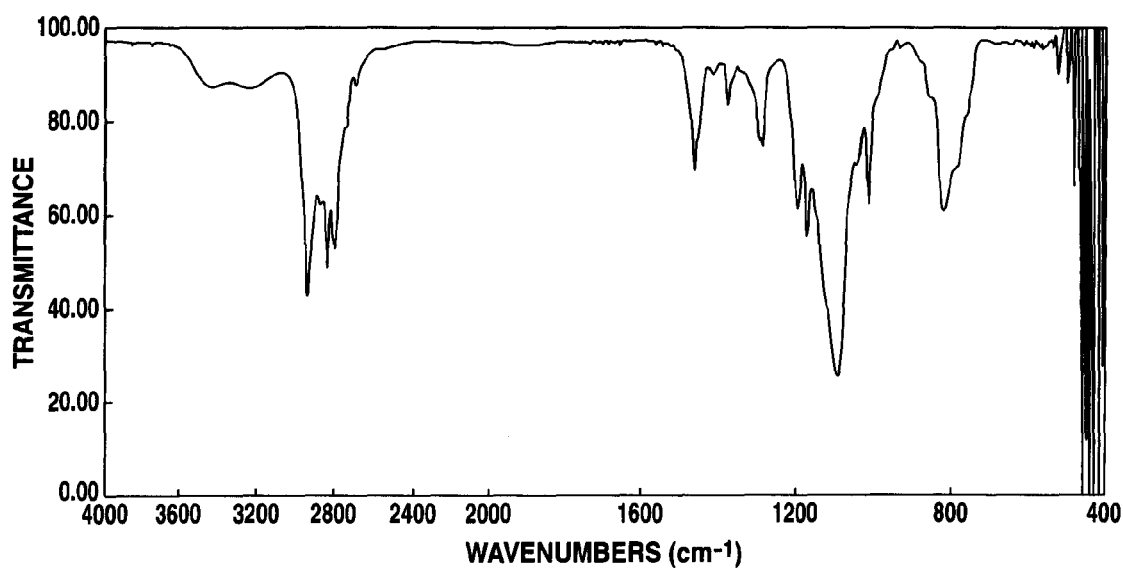
FIG. 2 is the IR spectrum of the composition produced in Synthetic Example 1.

The resulting composition was evaluated for $^1$H-NMR spectrum (deuterated chloroform solvent) and IR spectrum. FIG. 1 is the chart for the $^1$H-NMR spectrum, and FIG. 2 is the chart for the IR spectrum. Mass spectrum was also measured after silylating the resulting composition with bis(trimethylsilyl)trifluoroacetamide. The results of the mass spectrum are shown below.

Mass spectrum 1:

m/z 408, 393, 318, 229, 121, 113

Mass spectrum 2:

m/z 304, 273, 234, 139, 113

Mass spectrum 3:

m/z 712, 640, 393, 318, 229, 121

Mass spectrum 4:

m/z 608, 593, 318, 273, 121, 113

These results confirmed that the resulting composition was a mixed composition containing the compounds of the following formulae (7) to (10):

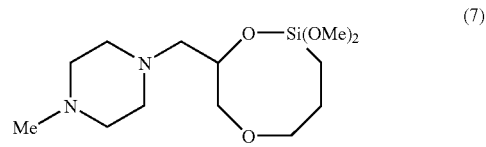

(7)

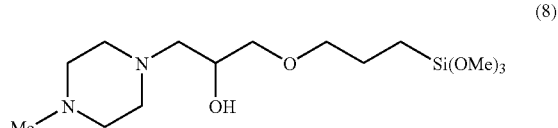

(8)

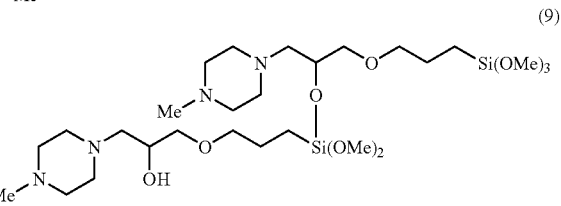

(9)

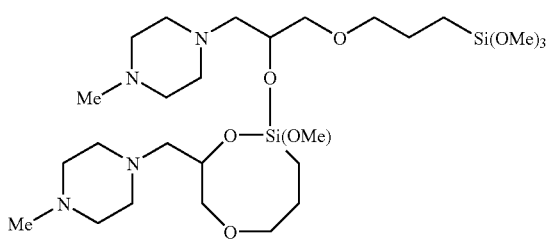

The resulting composition after the silylation was also analyzed by gas chromatography. Weight ratio of the compounds of formulae (7) to (10), namely, the compound of the formula (7):the compound of the formula (8):the compound of the formula (9):the compound of the formula (10) in the mixed composition was confirmed to be 20:46:7:27.

Example 1

Isolation of 1,1-dimethoxy-3-(4-methylpiperadino)methyl-2,5-dioxa-1-silacyclooctane The composition obtained in Synthetic Example 1 was distilled to obtain 39 g of a transparent fraction having a boiling point of 140 to 142° C. at 0.4 kPa.

Figure 3:
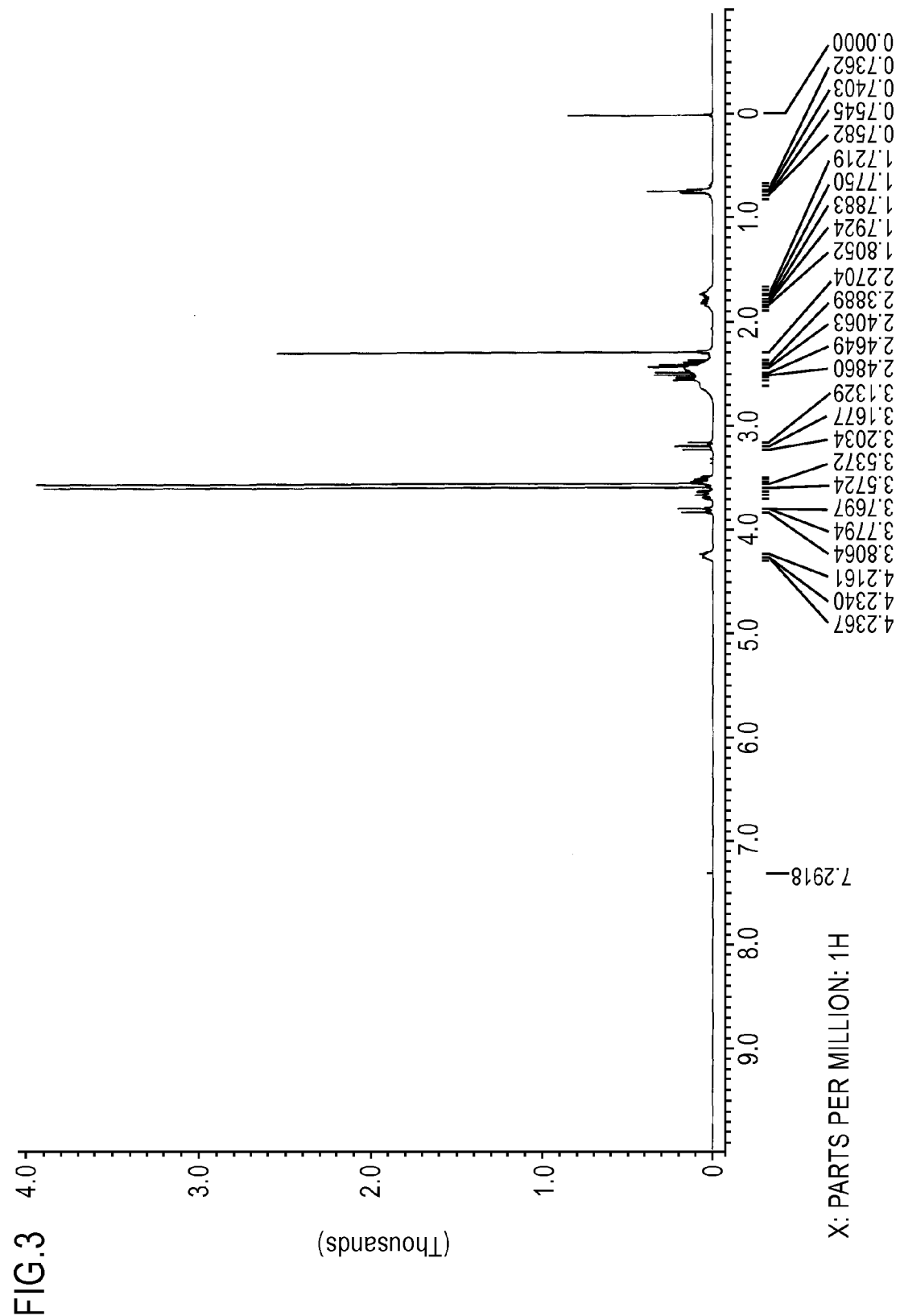
FIG. 3 is the $^1$H-NMR spectrum of the organosilicon compound produced in Example 1.
Figure 4:
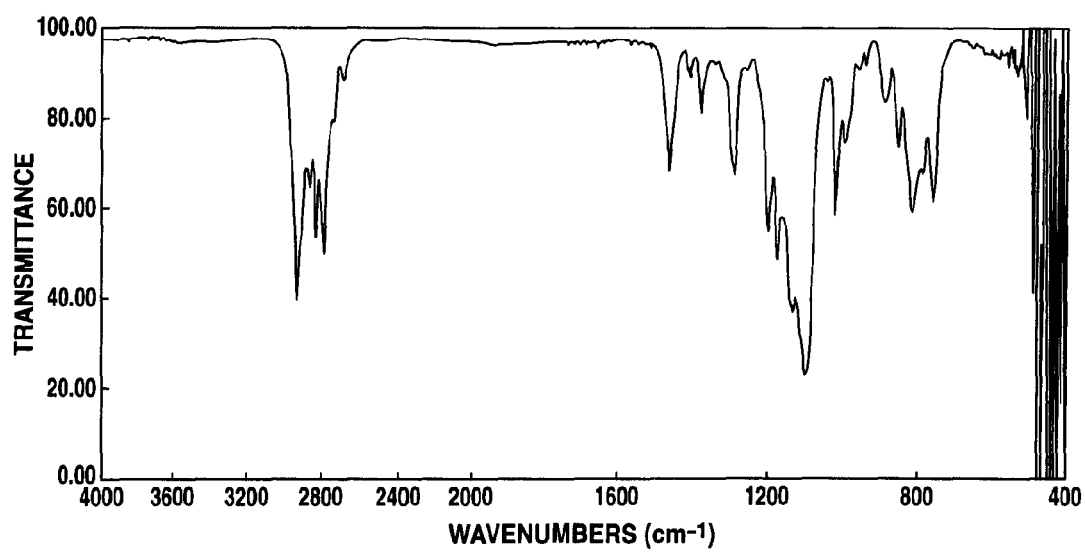
FIG. 4 is the IR spectrum of the organosilicon compound produced in Example 1.

The thus obtained fraction was evaluated by mass spectrum, $^1$H-NMR spectrum (deuterated chloroform solvent), and IR spectrum. The results of the mass spectrum are as shown below. FIG. 3 is the chart for the $^1$H-NMR spectrum, and FIG. 4 is the chart for the IR spectrum.

Mass spectrum:
m/z 304, 273, 234, 139, 113

These results confirmed that the resulting compound was the compound of the formula (7).

Example 2

Methanol-Containing Composition of the Compound of Example 1

The compound represented by the general formula (7) obtained in Example 1 was mixed with an equal weight of methanol to prepare a methanol-containing composition. The resulting methanol-containing composition could be stored at room temperature for more than 1 month without gelation and without losing its transparency.

Example 3

Water-Containing Composition of the Compound of Example 1

The compound represented by the general formula (7) obtained in Example 1 was mixed with an equal weight of water to prepare a water-containing composition. The resulting water-containing composition could be stored at room temperature for more than 1 month without gelation and without losing its transparency.

Synthetic Example 2

Reaction of methylpiperazine and γ-glycidoxypropylmethyl-diethoxysilane

A flask equipped with a stirrer, a reflux condenser, a dropping funnel, and a thermometer was charged with 20 g (0.20 mole) of methylpiperazine, and 50 g (0.20 mole) of γ-glycidoxypropylmethyldiethoxysilane was added dropwise at 90 to 100° C. for 6 hours, and the mixture was stirred at the same temperature for 2 hours to obtain a transparent composition.

Figure 5:
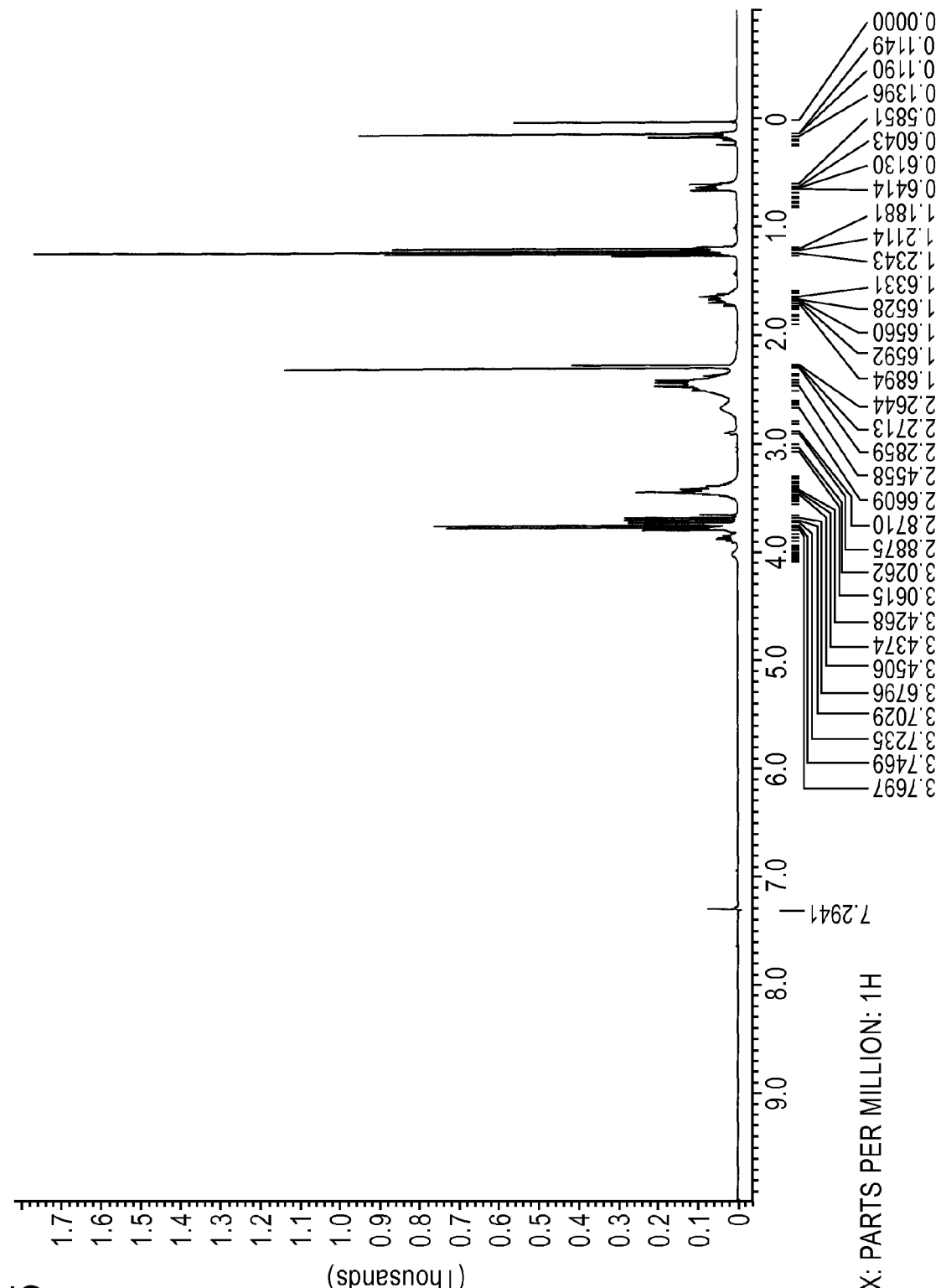
FIG. 5 is the $^1$H-NMR spectrum of the composition produced in Synthetic Example 2.
Figure 6:
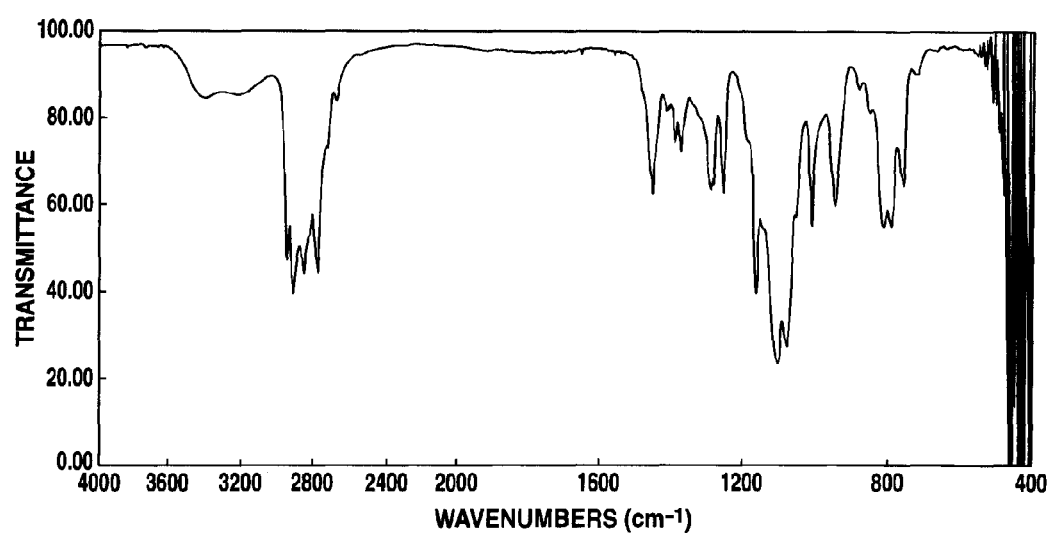
FIG. 6 is the IR spectrum of the composition produced in Synthetic Example 2.

The resulting composition was evaluated for $^1$H-NMR spectrum (deuterated chloroform solvent) and IR spectrum. FIG. 5 is the chart for the $^1$H-NMR spectrum, and FIG. 6 is the chart for the IR spectrum. Mass spectrum was also measured after silylating the resulting composition with bis(trimethylsilyl)trifluoroacetamide. The results of the mass spectrum are shown below.

Mass spectrum 1:
m/z 420, 405, 330, 229, 133, 113
Mass spectrum 2:
m/z 302, 287, 257, 139, 113
Mass spectrum 3:
m/z 722, 650, 391, 330, 229, 133
Mass spectrum 4:
m/z 604, 589, 559, 330, 257, 113

These results confirmed that the resulting composition was a mixed composition containing the compounds of the following formulae (11) to (14):

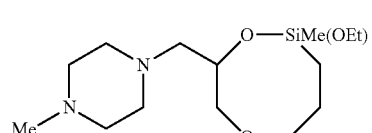

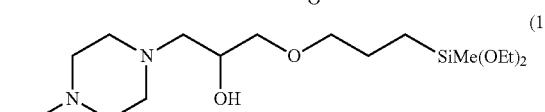

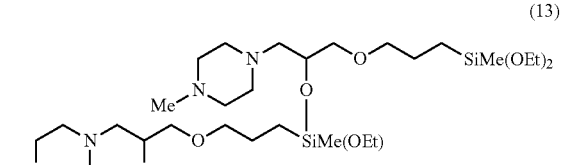

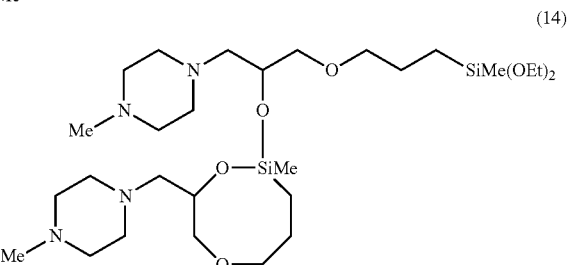

The resulting composition after the silylation was also analyzed by gas chromatography. Weight ratio of the compounds of formulae (11) to (14), namely, the compound of the formula (11):the compound of the formula (12):the compound of the formula (13):the compound of the formula (14) in the mixed composition was confirmed to be 5:64:30:1.

Example 4

Isolation of 1-ethoxy-1-methyl-3-(4-methylpiperadino)-methyl-2,5-dioxa-1-silacyclooctane The composition obtained in Synthetic Example 2 was distilled to obtain 12 g of a transparent fraction having a boiling point of 133 to 135° C. at 0.3 kPa.

Figure 7:
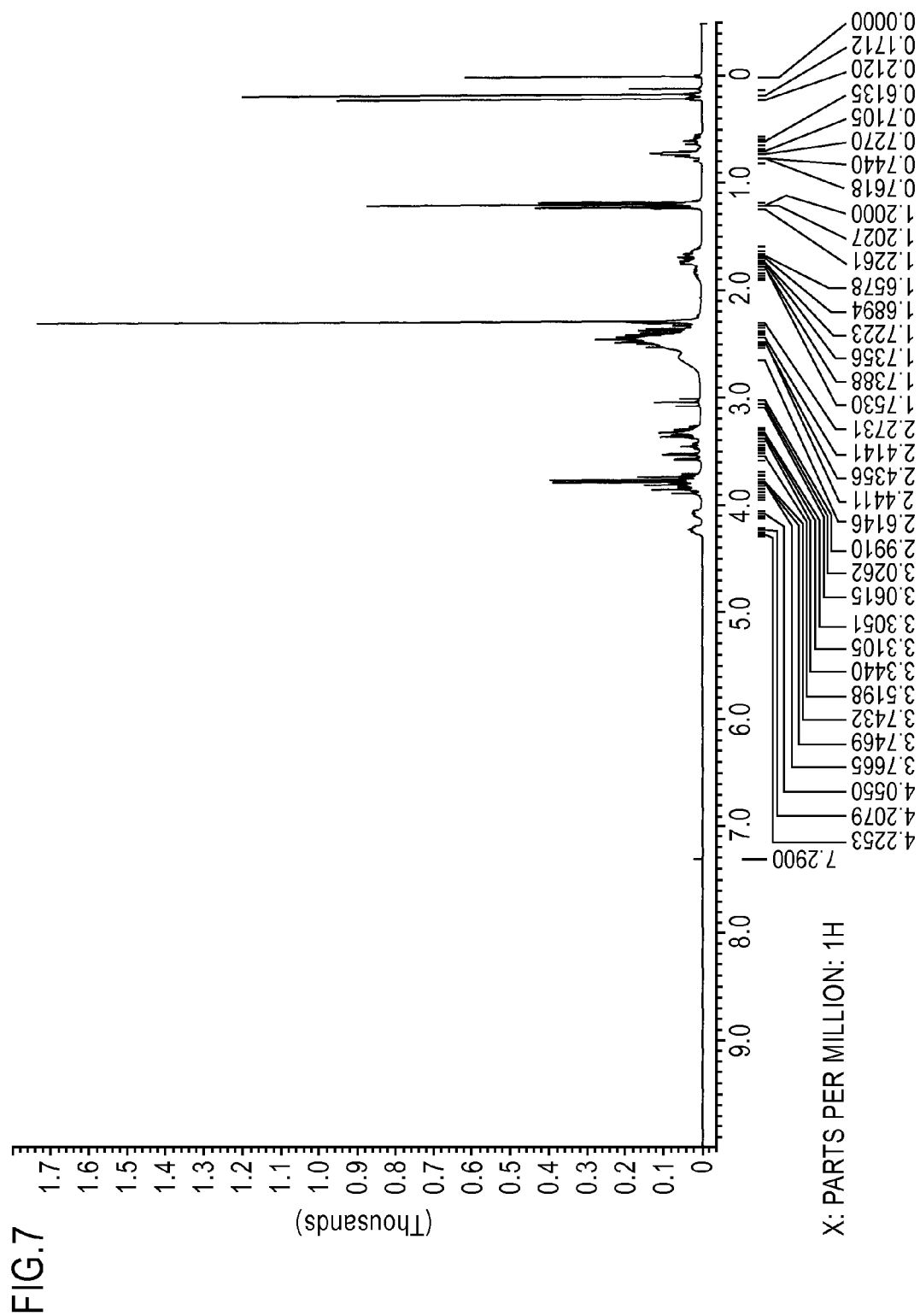
FIG. 7 is the $^1$H-NMR spectrum of the organosilicon compound produced in Example 4.
Figure 8:
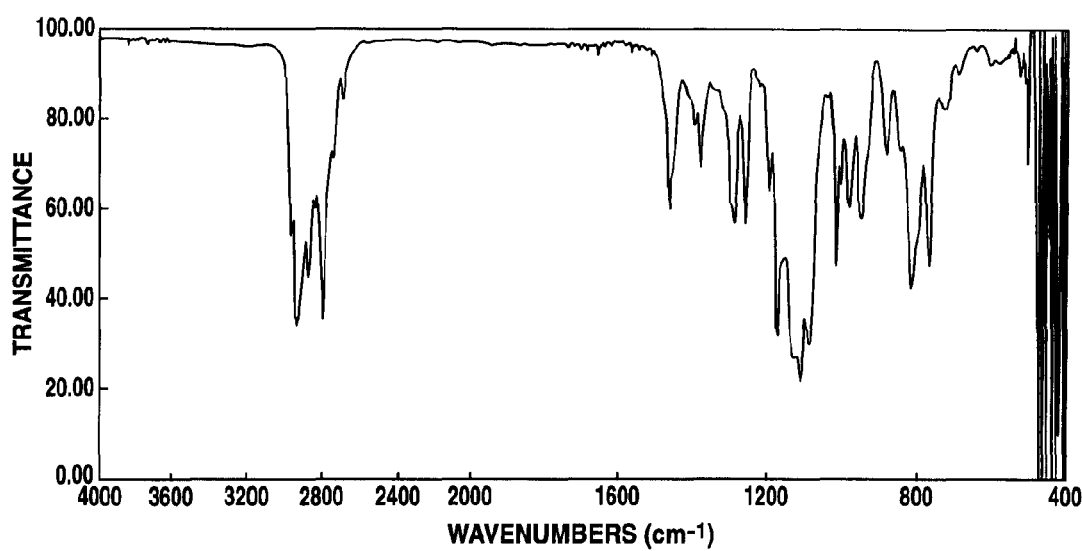
FIG. 8 is the IR spectrum of the organosilicon compound produced in Example 4.

The thus obtained fraction was evaluated by mass spectrum, $^1$H-NMR spectrum (deuterated chloroform solvent), and IR spectrum. The results of the mass spectrum are as shown below. FIG. 7 is the chart for the $^1$H-NMR spectrum, and FIG. 8 is the chart for the IR spectrum.

Mass spectrum:
m/z 302, 287, 257, 139, 113

These results confirmed that the resulting compound was the compound of the formula (11).

Example 5

Ethanol-Containing Composition of the Compound of Example 4

The compound represented by the general formula (11) obtained in Example 3 was mixed with an equal weight of ethanol to prepare an ethanol-containing composition. The resulting ethanol-containing composition could be stored at room temperature for more than 1 month without gelation and without losing its transparency.

Example 6

Water-Containing Composition of the Compound of Example 4

The compound represented by the general formula (11) obtained in Example 4 was mixed with an equal weight of water to prepare a water-containing composition. The resulting water-containing composition could be stored at room temperature for more than 1 month without gelation and without losing its transparency.

Synthetic Example 3

Reaction of diethylamine and γ-glycidoxypropylmethyl-dimethoxysilane

A flask equipped with a stirrer, a reflux condenser, a dropping funnel, and a thermometer was charged with 16 g (0.22 mole) of diethylamine, and 44 g (0.20 mole) of γ-glycidoxypropylmethyldimethoxysilane was added dropwise at 57 to 98° C. for 10 hours, and the mixture was stirred at the same temperature for 3 hours to obtain a transparent composition.

Figure 9:
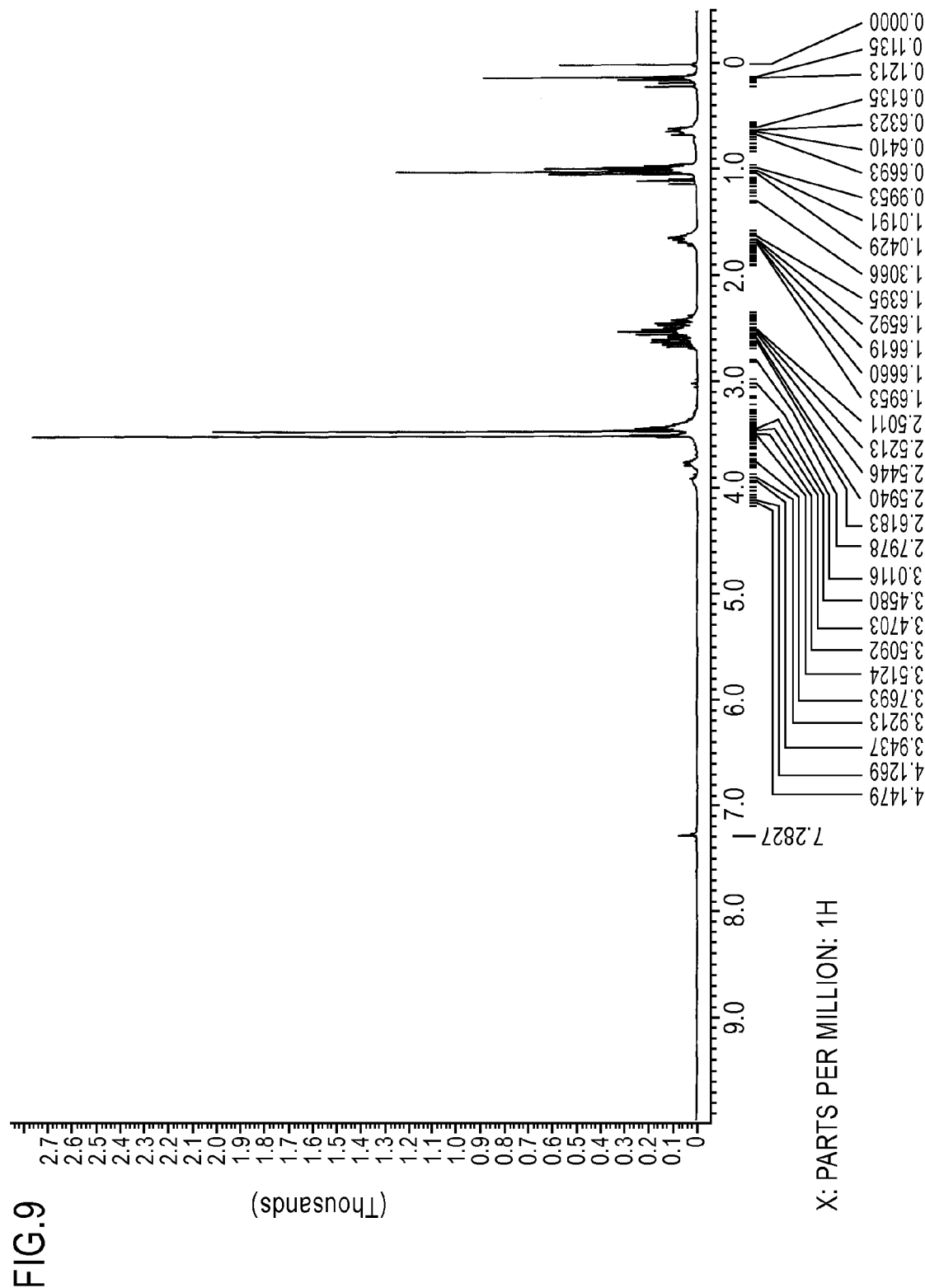
FIG. 9 is the $^1$H-NMR spectrum of the composition produced in Synthetic Example 3.
Figure 10:
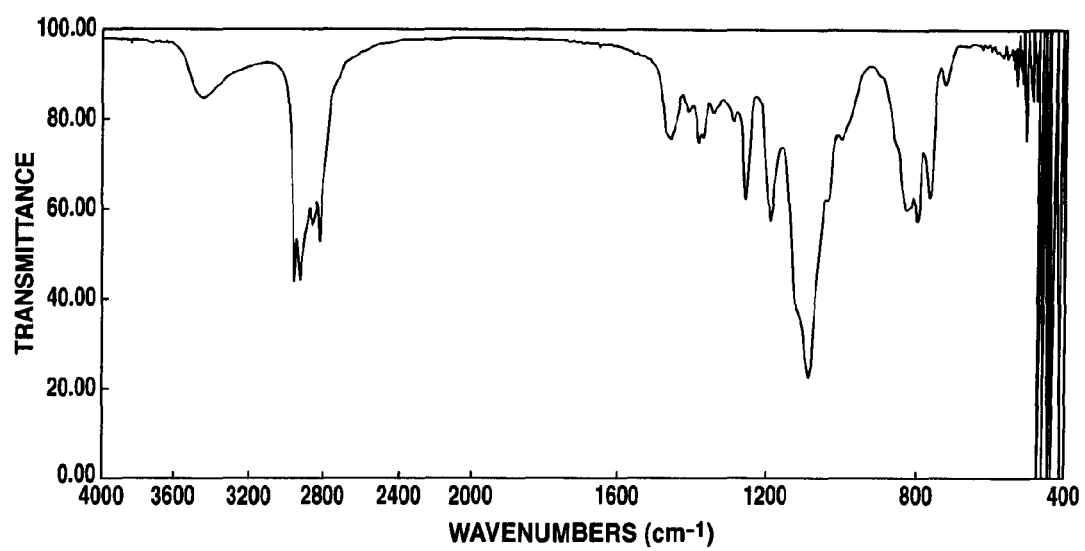
FIG. 10 is the IR spectrum of the composition produced in Synthetic Example 3.

The resulting composition was evaluated for $^1$H-NMR spectrum (deuterated chloroform solvent) and IR spectrum. FIG. 9 is the chart for the $^1$H-NMR spectrum, and FIG. 10 is the chart for the IR spectrum. Mass spectrum was also measured after silylating the resulting composition with bis(trimethylsilyl)trifluoroacetamide. The results of the mass spectrum are shown below.

Mass spectrum 1:
m/z 350, 275, 202, 105, 86

Mass spectrum 2:
m/z 261, 246, 218, 188, 86

Mass spectrum 3:
m/z 611, 597, 352, 275, 202, 86

Mass spectrum 4:
m/z 507, 493, 322, 262, 230, 86

These results confirmed that the resulting composition was a mixed composition containing the compounds of the following formulae (15) to (18):

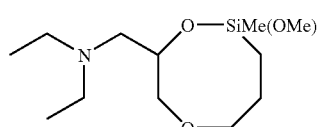

(15)

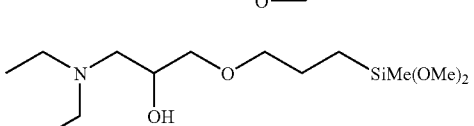

(16)

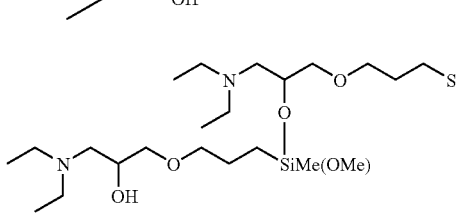

(17)

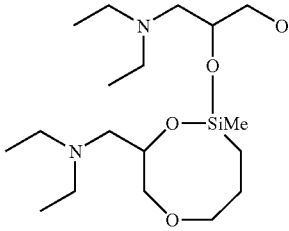

(18)

The resulting composition after the silylation was also analyzed by gas chromatography. Weight ratio of the compounds of formulae (15) to (18), namely, the compound of the formula (15):the compound of the formula (16):the compound of the formula (17):the compound of the formula (18) in the mixed composition was confirmed to be 11:53:35:1.

Example 7

Isolation of 1-methoxy-1-methyl-3-diethylaminomethyl-2,5-dioxa-1-silacyclooctane The composition obtained in Synthetic Example 3 was distilled to obtain 12 g of a transparent fraction having a boiling point of 105° C. at 0.2 kPa.

Figure 11:
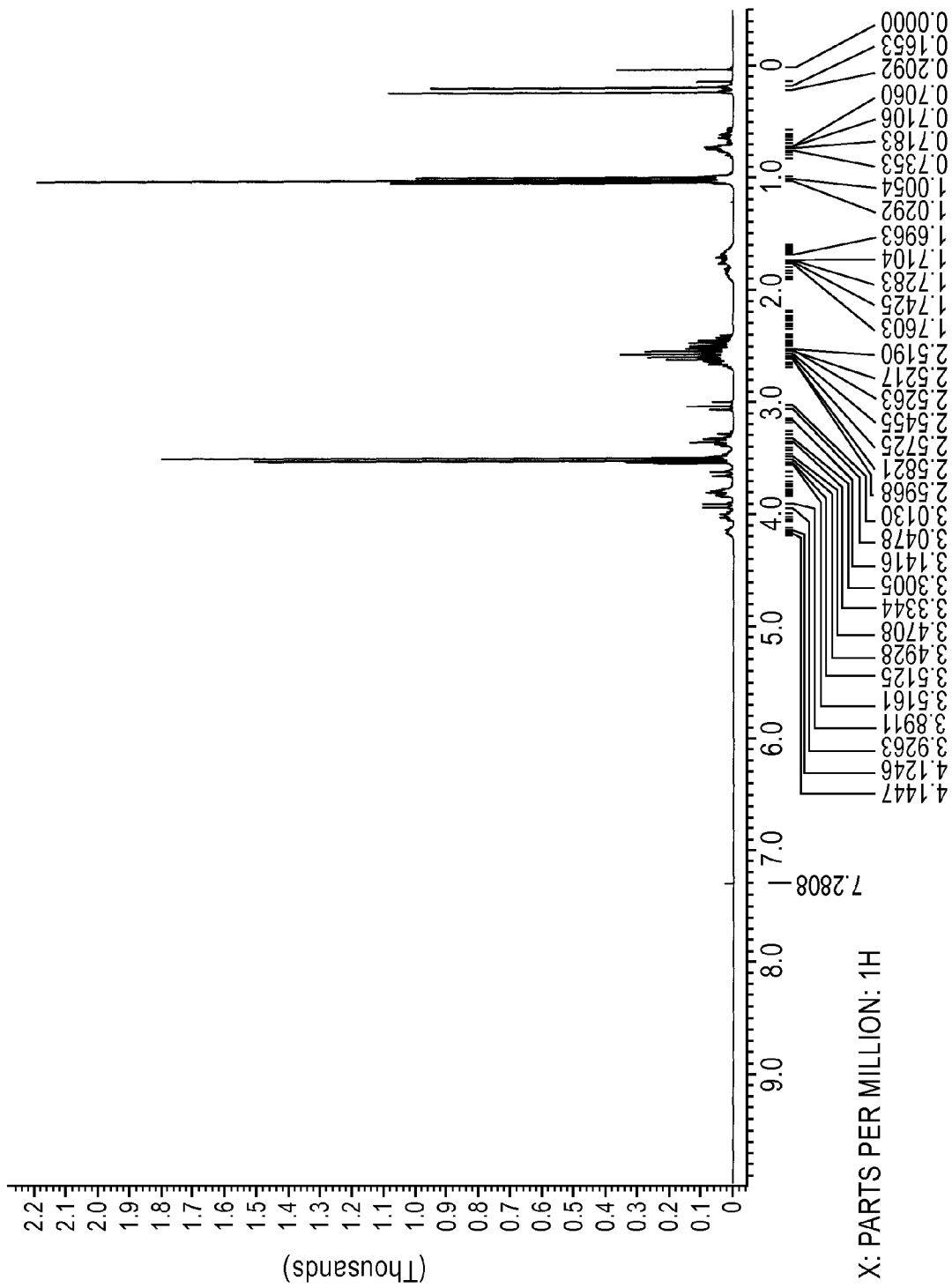
FIG. 11 is the $^1$H-NMR spectrum of the organosilicon compound produced in Example 7.
Figure 12:
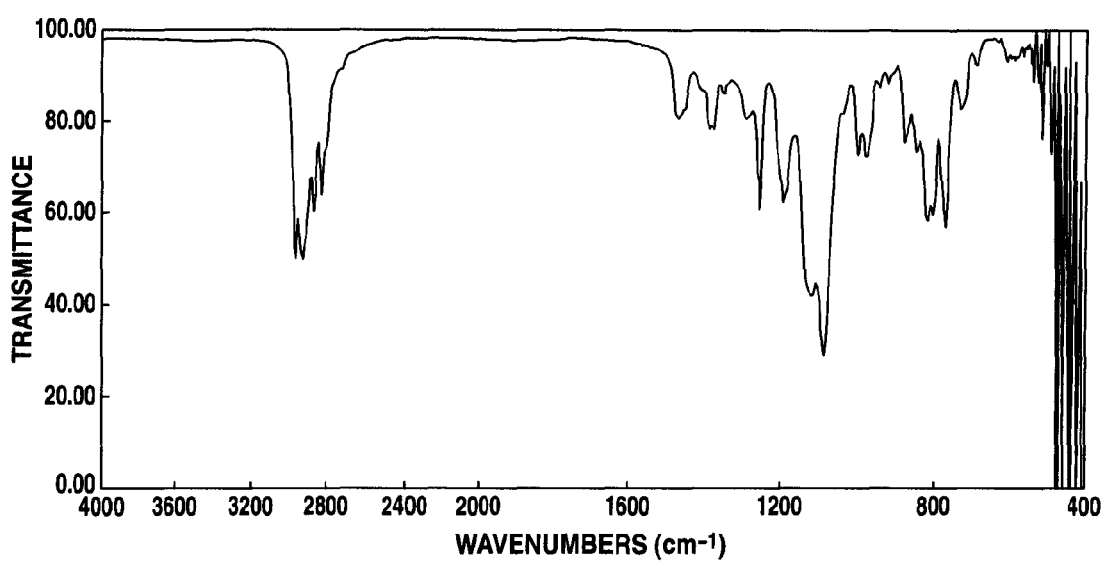
FIG. 12 is the IR spectrum of the organosilicon compound produced in Example 7.

The thus obtained fraction was evaluated by mass spectrum, $^1$H-NMR spectrum (deuterated chloroform solvent), and IR spectrum. The results of the mass spectrum are as shown below. FIG. 11 is the chart for the $^1$H-NMR spectrum, and FIG. 12 is the chart for the IR spectrum.

Mass spectrum:
m/z 261, 246, 218, 188, 86

These results confirmed that the resulting compound was the compound of the formula (15).

Example 8

Methanol-Containing Composition of the Compound of Example 7

The compound represented by the general formula (15) obtained in Example 7 was mixed with an equal weight of methanol to prepare a methanol-containing composition. The resulting methanol-containing composition could be stored at room temperature for more than 1 month without gelation and without losing its transparency.

Example 9

A flask equipped with a stirrer, a Dean-Stark trap, a reflux condenser, a dropping funnel, and a thermometer was charged with 60 g (0.60 mole) of methylpiperazine and 300 mL of toluene, and 94 g (0.40 mole) of γ-glycidoxypropyltrimethoxysilane was added dropwise while refluxing the toluene. The dropwise addition was continued for 10 hours while gradually removing the fraction containing the alcohol from the Dean-Stark trap, and during the addition, internal temperature of the flask was maintained at 116 to 119° C. Removal of the fraction was continued until the internal temperature was 140° C., and the reaction was completed. The resulting reaction mixture was a mixed composition containing the compounds general formulae (7) to (10), and analysis by gas chromatography confirmed that weight ratio of the compounds of formulae (7) to (10), namely, the compound of the formula (7):the compound of the formula (8):the compound of the formula (9):the compound of the formula (10) in the mixed composition was 60:4:8:28. The reaction mixture was distilled to obtain 59 g of a fraction having a boiling point of 140 to 141° C. at 0.4 kPa.

Figure 13:
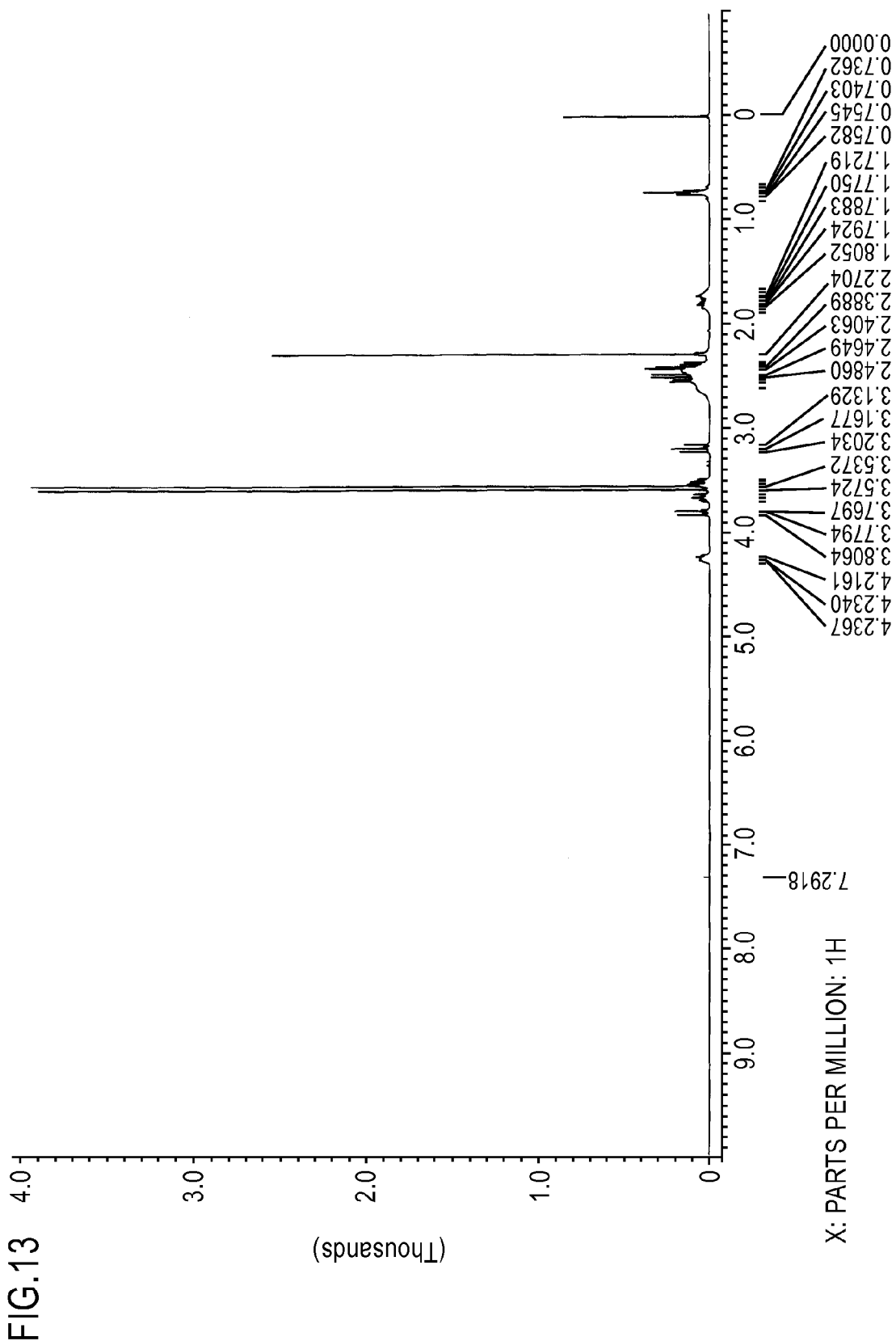
FIG. 13 is the $^1$H-NMR spectrum of the organosilicon compound produced in Example 9.
Figure 14:
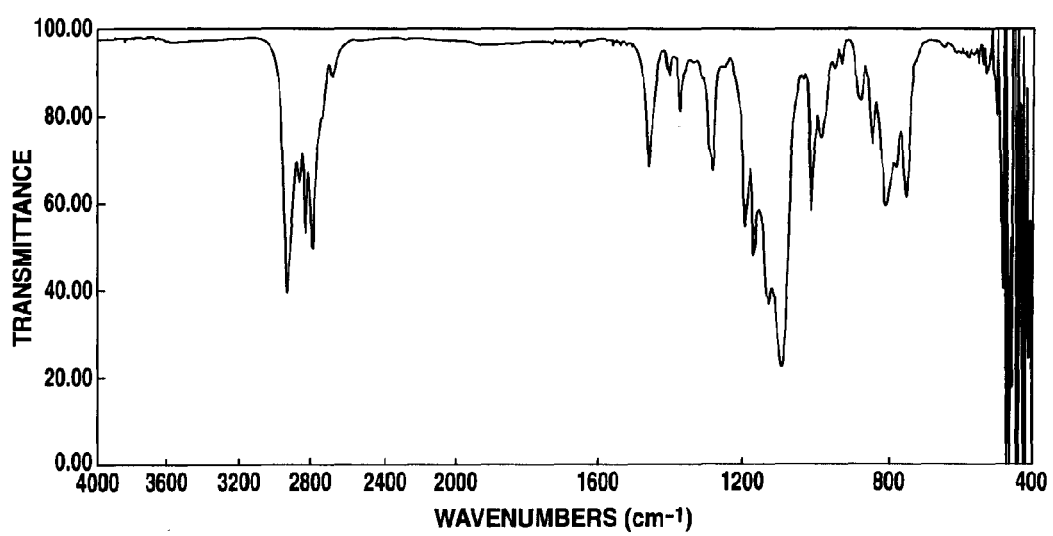
FIG. 14 is the IR spectrum of the organosilicon compound produced in Example 9.

The thus obtained fraction was evaluated by mass spectrum, $^1$H-NMR spectrum (deuterated chloroform solvent), and IR spectrum. The results of the mass spectrum are as shown below. FIG. 13 is the chart for the $^1$H-NMR spectrum, and FIG. 14 is the chart for the IR spectrum.

Mass spectrum:
m/z 304, 273, 234, 139, 113

These results confirmed that the resulting compound was 1,1-dimethoxy-3-(4-methylpiperadino)methyl-2,5-dioxa-1-silacyclooctane, and the yield in terms of silicon was 48%.

Example 10

A flask equipped with a stirrer, a thermometer, a packed column equipped at its upper end with a dropping funnel, a Dean-Stark trap, and a reflux condenser, and a thermometer was charged with 150 g (1.50 mole) of methylpiperazine and 60 g (0.30 mole) of γ-glycidoxypropyltrimethoxysilane was added dropwise while refluxing the methylpiperazine. The dropwise addition was continued for 10 hours while gradually removing the methylpiperazine containing the alcohol from the Dean-Stark trap, and during the addition, internal temperature of the flask was maintained at 140 to 149° C. The resulting reaction mixture was a mixed composition containing the compounds general formulae (7) to (10), and analysis by gas chromatography confirmed that weight ratio of the compounds of formulae (7) to (10), namely, the compound of the formula (7):the compound of the formula (8):the compound of the formula (9):the compound of the formula (10) in the mixed composition was 71:6:4:19. The reaction mixture was distilled to obtain 68 g of a fraction having a boiling point of 140 to 141° C. at 0.4 kPa.

The thus obtained fraction was evaluated by mass spectrum, $^1$H-NMR spectrum (deuterated chloroform solvent), and IR spectrum. The results confirmed that the resulting compound was 1,1-dimethoxy-3-(4-methylpiperadino)methyl-2,5-dioxa-1-silacyclooctane, and the yield in terms of silicon was 75%.

Example 11

The procedure of Example 9 was repeated except that 1.5 g of solution of sodium methoxide in methanol (28% by weight of sodium methoxide) was added to the flask during the reaction. The resulting reaction mixture was a mixed composition containing the compounds general formulae (7) to (10), and analysis by gas chromatography confirmed that weight ratio of the compounds of formulae (7) to (10), namely, the compound of the formula (7):the compound of the formula (8):the compound of the formula (9):the compound of the formula (10) in the mixed composition was 68:2:6:24. The reaction mixture was distilled to obtain 102 g of a fraction having a boiling point of 140 to 141° C. at 0.4 kPa.

The thus obtained fraction was evaluated by mass spectrum, $^1$H-NMR spectrum (deuterated chloroform solvent), and IR spectrum. The results confirmed that the resulting compound was 1,1-dimethoxy-3-(4-methylpiperadino)methyl-2,5-dioxa-1-silacyclooctane, and the yield in terms of silicon was 84%.

Example 12

The procedure of Example 9 was repeated, and in the distillation of the resulting reaction mixture, 1.5 g of solution of sodium methoxide in methanol (28% by weight of sodium methoxide) was added to the distillation tank to obtain 84 g of a fraction having a boiling point of 140 to 141° C. at 0.4 kPa.

The thus obtained fraction was evaluated by mass spectrum, $^1$H-NMR spectrum (deuterated chloroform solvent), and IR spectrum. The results confirmed that the compound was 1,1-dimethoxy-3-(4-methylpiperadino)methyl-2,5-dioxa-1-silacyclooctane, and the yield in terms of silicon was 69%.

Example 13

A flask equipped with a stirrer, a Dean-Stark trap, a reflux condenser, a dropping funnel, and a thermometer was charged with 52 g (0.60 mole) of morpholine, 300 mL of toluene, and 1.5 g of solution of sodium methoxide in methanol (28% by weight of sodium methoxide), and 94 g (0.40 mole) of γ-glycidoxypropyltrimethoxysilane was added dropwise while refluxing the toluene. The dropwise addition was continued for 8 hours while gradually removing the fraction containing the alcohol from the Dean-Stark trap, and during the addition, internal temperature of the flask was maintained at 116 to 119° C. Removal of the fraction was continued until the internal temperature was 140° C., and the reaction was completed. The resulting reaction mixture was a mixed composition containing the compounds general formulae (19) to (22), and analysis by gas chromatography confirmed that weight ratio of the compounds of formulae (19) to (22), namely, the compound of the formula (19):the compound of the formula (20):the compound of the formula (21): the compound of the formula (22) in the mixed composition was 52:6:10:32. The reaction mixture was distilled to obtain 59 g of a fraction having a boiling point of 134 to 136° C. at 0.3 kPa.

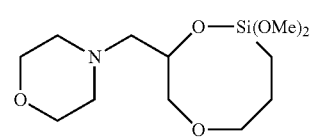

(19)

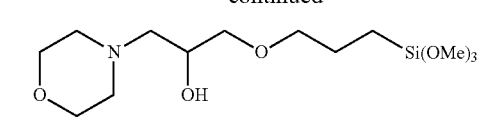
(20)

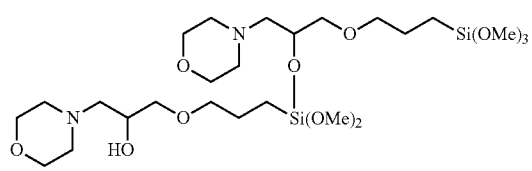
(21)

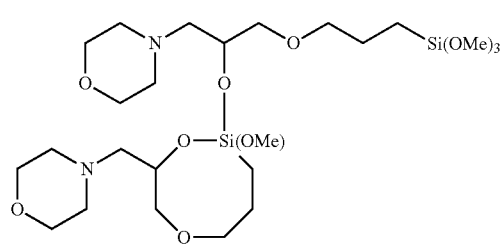
(22)

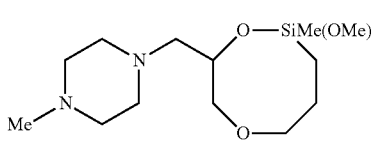
(23)

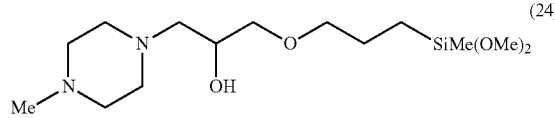
(24)

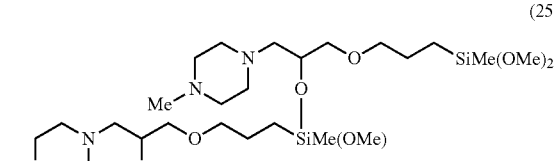
(25)

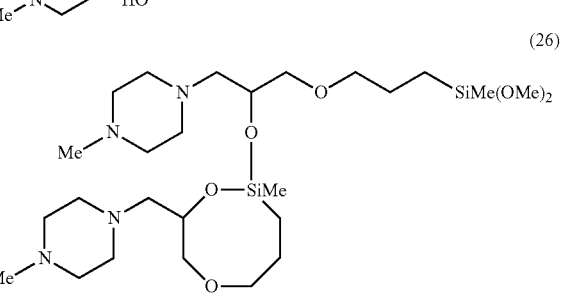
(26)

Figure 15:
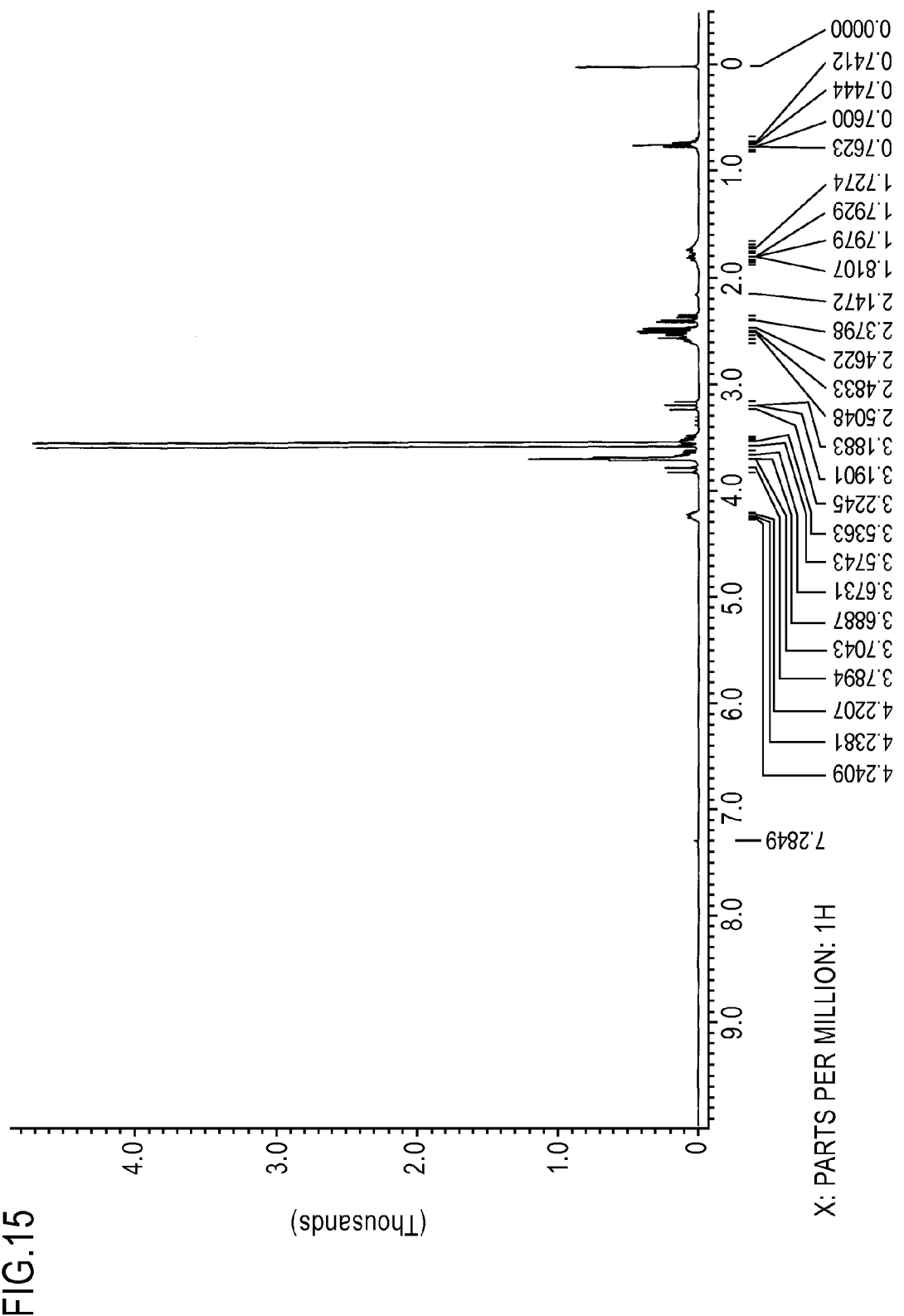
FIG. 15 is the $^1$H-NMR spectrum of the organosilicon compound produced in Example 13.
Figure 16:
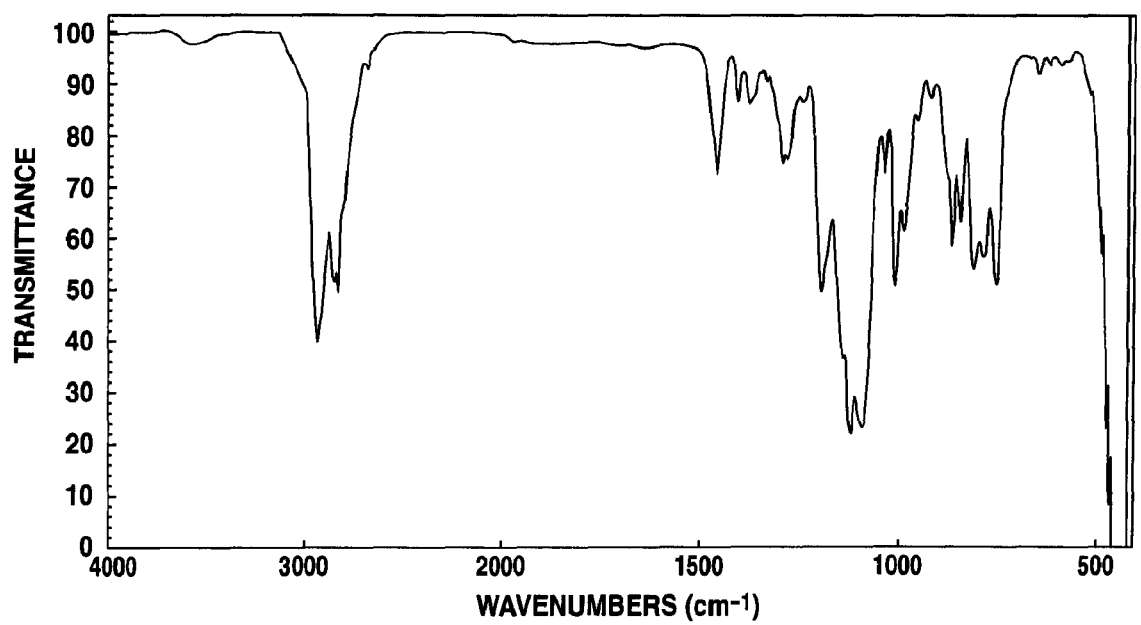
FIG. 16 is the IR spectrum of the organosilicon compound produced Example 13.

The thus obtained fraction was evaluated by mass spectrum, $^1$H-NMR spectrum (deuterated chloroform solvent), and IR spectrum. The results of the mass spectrum are as shown below. FIG. 15 is the chart for the $^1$H-NMR spectrum, and FIG. 16 is the chart for the IR spectrum.

Mass spectrum:

m/z 291, 260, 204, 163, 100

These results confirmed that the resulting compound was 1,1-dimethoxy-3-morpholinomethyl-2,5-dioxa-1-silacyclooctane, and the yield in terms of silicon was 53%.

Example 14

A flask equipped with a stirrer, a Dean-Stark trap, a reflux condenser, a dropping funnel, and a thermometer was charged with 60 g (0.60 mole) of methylpiperazine, 300 mL of toluene, and 1.5 g of solution of sodium methoxide in methanol (28% by weight of sodium methoxide), and 88 g (0.40 mole) of γ-glycidoxypropylmethyldimethoxysilane was added dropwise while refluxing the toluene. The dropwise addition was continued for 8 hours while gradually removing the fraction containing the alcohol from the Dean-Stark trap, and during the addition, internal temperature of the flask was maintained at 116 to 119° C. Removal of the fraction was continued until the internal temperature was 150° C., and the reaction was completed. The resulting reaction mixture was a mixed composition containing the compounds general formulae (23) to (26), and analysis by gas chromatography confirmed that weight ratio of the compounds of formulae (23) to (26), namely, the compound of the formula (23):the compound of the formula (24):the compound of the formula (25):the compound of the formula (26) in the mixed composition was 56:4:1:28. The reaction mixture was distilled to obtain 80 g of a fraction having a boiling point of 128 to 130° C. at 0.2 kPa.

Figure 17:
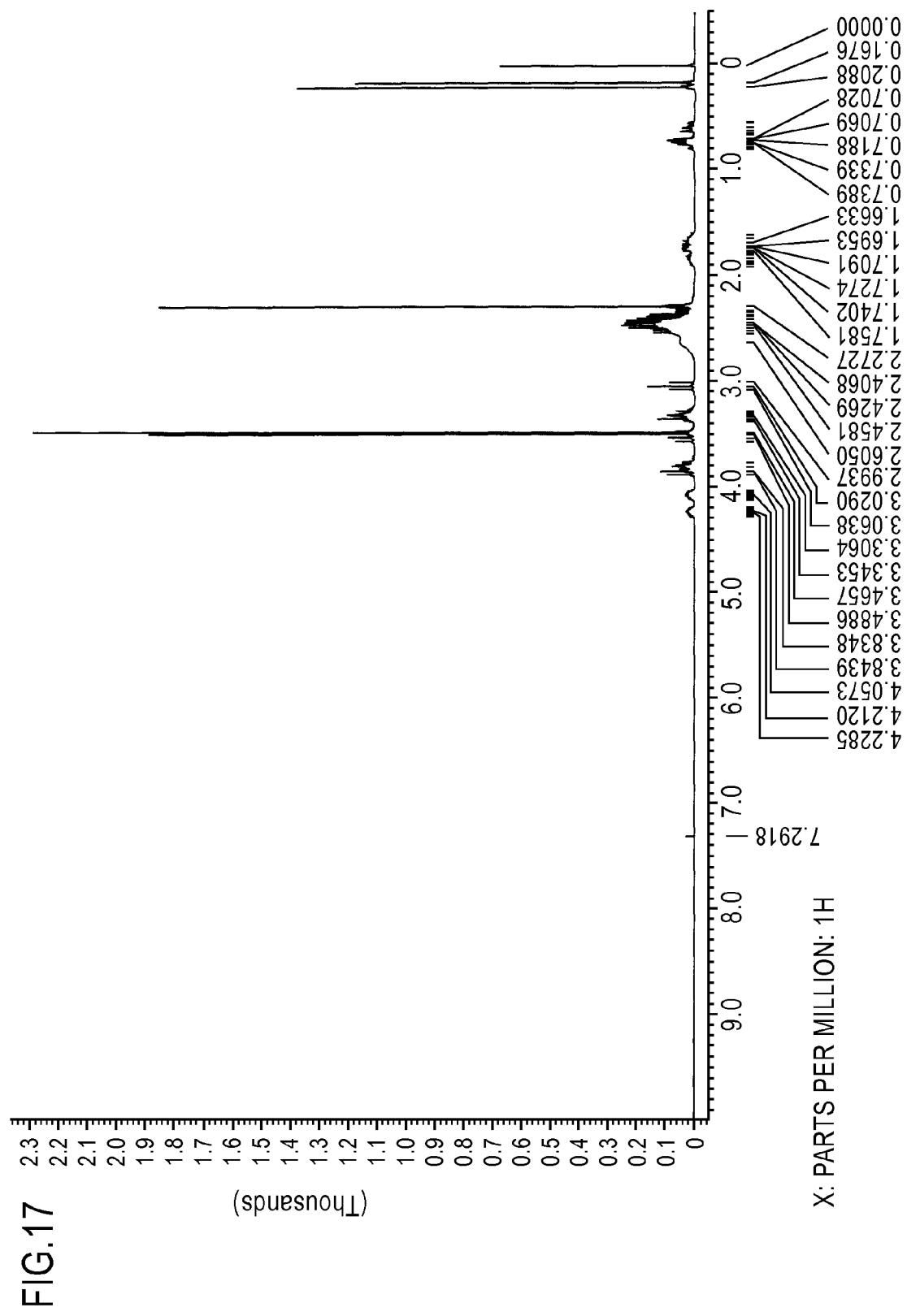
FIG. 17 is the $^1$H-NMR spectrum of the organosilicon compound produced in Example 14.
Figure 18:
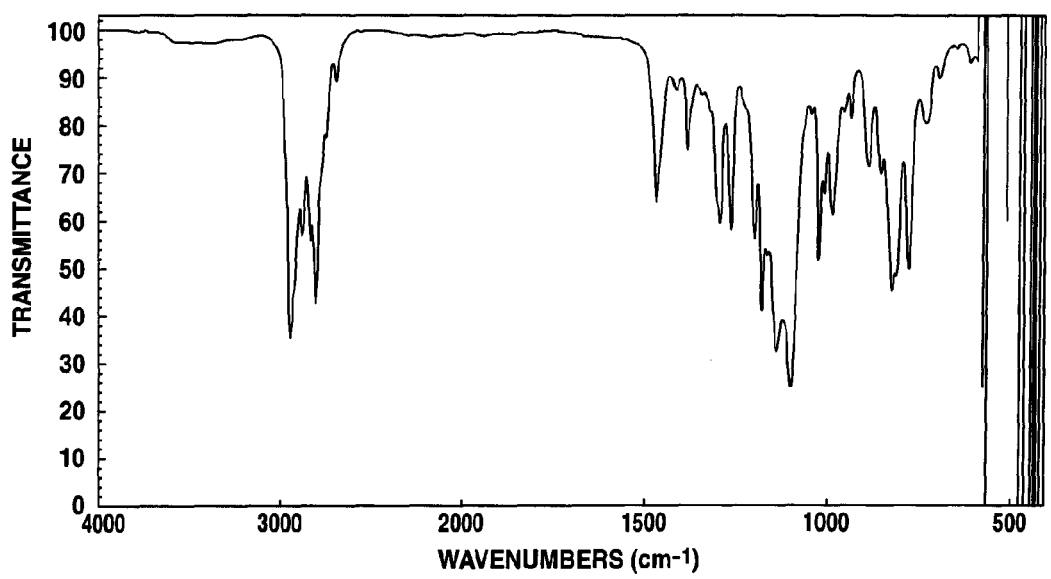
FIG. 18 is the IR spectrum of the organosilicon compound produced Example 14.

The thus obtained fraction was evaluated by mass spectrum, $^1$H-NMR spectrum (deuterated chloroform solvent), and IR spectrum. The results of the mass spectrum are as shown below. FIG. 17 is the chart for the $^1$H-NMR spectrum, and FIG. 18 is the chart for the IR spectrum.

Mass spectrum:

m/z 288, 273, 257, 175, 113

These results confirmed that the resulting compound was 1-methoxy-1-methyl-3-(4-methylpiperadino)methyl-2,5-dioxa-1-silacyclooctane, and the yield in terms of silicon was 69%.

Example 15

A flask equipped with a stirrer, a Dean-Stark trap, a reflux condenser, a dropping funnel, and a thermometer was charged with 60 g (0.60 mole) of methylpiperazine, 300 mL of toluene, and 2.7 g of solution of sodium ethoxide in ethanol (20% by weight sodium ethoxide), and 111 g (0.40 mole) of γ-glycidoxypropyltriethoxysilane was added dropwise while refluxing the toluene. The dropwise addition was continued for 7 hours while gradually removing the fraction containing the alcohol from the Dean-Stark trap, and during the addition, internal temperature of the flask was maintained at 116 to 119° C. Removal of the fraction was continued until the internal temperature was 145° C., and the reaction was completed. The resulting reaction mixture was a mixed composition containing the compounds general formulae (27) to (30), and analysis by gas chromatography confirmed that weight ratio of the compounds of formulae (27) to (30), namely, the compound of the formula (27):the compound of the formula (28):the compound of the formula (29):the compound of the formula (30) in the mixed composition was 56:4:10:30. The reaction mixture was distilled to obtain 107 g of a fraction having a boiling point of 145 to 147° C. at 0.2 kPa.

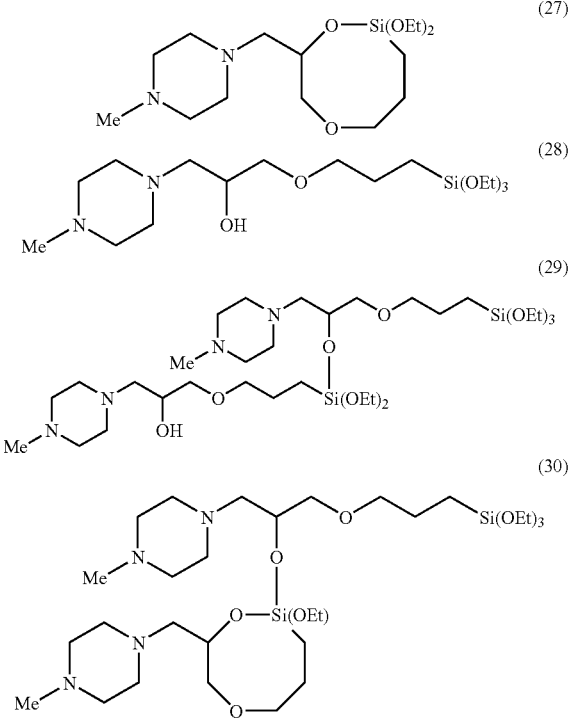

Figure 19:
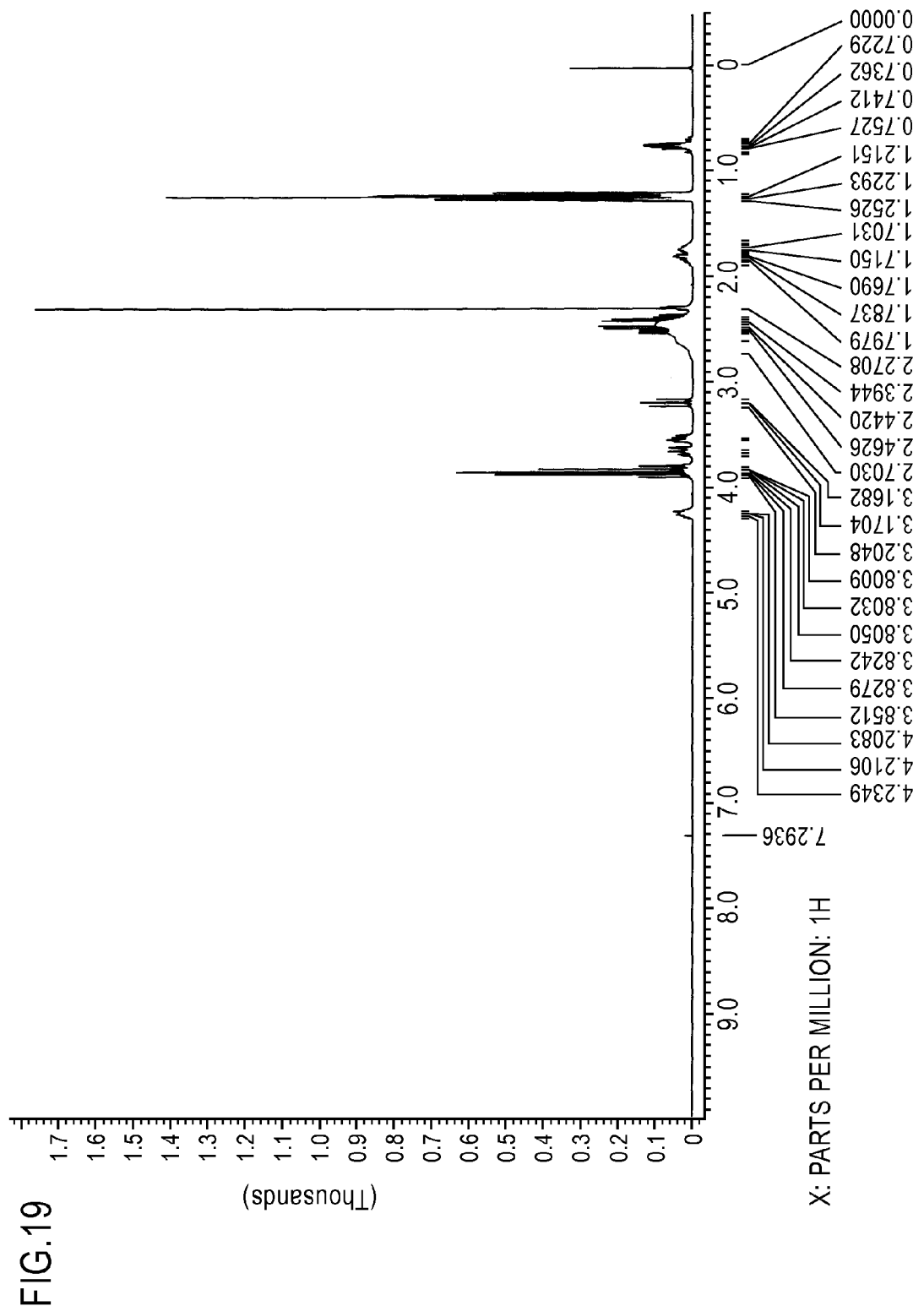
FIG. 19 is the $^1$H-NMR spectrum of the organosilicon compound produced in Example 15.
Figure 20:
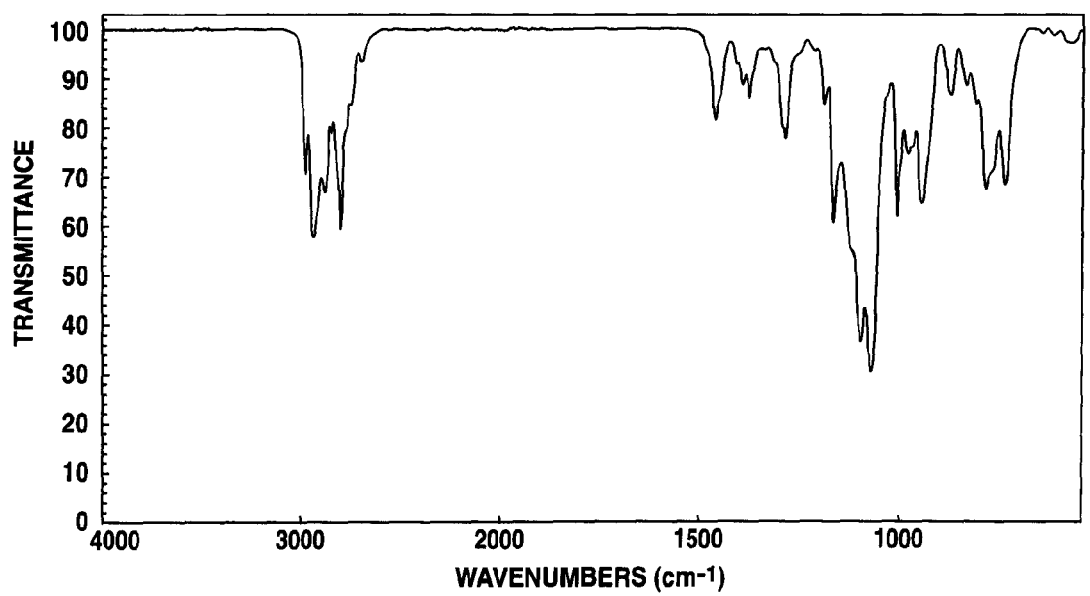
FIG. 20 is the IR spectrum of the organosilicon compound produced in Example 15.

The thus obtained fraction was evaluated by mass spectrum, $^1$H-NMR spectrum (deuterated chloroform solvent), and IR spectrum. The results of the mass spectrum are as shown below. FIG. 19 is the chart for the $^1$H-NMR spectrum, and FIG. 20 is the chart for the IR spectrum.

Mass spectrum:
m/z 332, 287, 262, 139, 113

These results confirmed that the resulting compound was 1,1-diethoxy-3-(4-methylpiperadino)methyl-2,5-dioxa-1-silacyclooctane, and the yield in terms of silicon was 78%.

Japanese Patent Application Nos. 2008-271643 and 2009-142152 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organosilicon compound having an amino group represented by the following general formula (1):

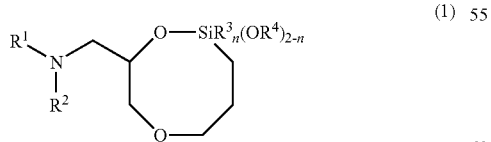

(1)

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2.

2. A method for producing an organosilicon compound having an amino group of claim 1 comprising the step of distilling a reaction mixture of an amine compound represented by the following general formula (2):

(2)

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; and n represents an integer of 0 to 2; with a γ-glycidoxypropylalkoxysilane represented by the following general formula (3):

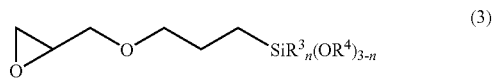

(3)

wherein $R^3$ and $R^4$ are independently an unsubstituted or substituted monovalent hydrocarbon group containing 1 to 10 carbon atoms, and n is an integer of 0 to 2.

3. A method according to claim 2 wherein 0.5 to 10 mole of the amine compound of the formula (2) is reacted per mole of the silane compound of the formula (3), and the reaction is conducted at a temperature of 50 to 200° C.

4. A mixture produced by the method of claim 2 wherein said mixture comprises a compound represented by the following general formula (1), a compound represented by the following general formula (4), a compound represented by the following general formula (5), and a the compound represented by the following general formula (6):

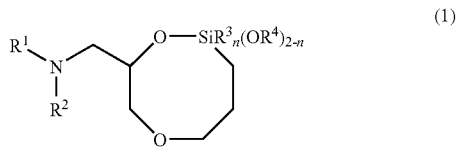

(1)

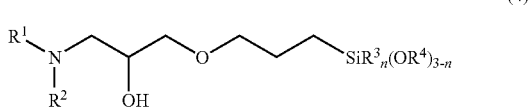

(4)

(5)

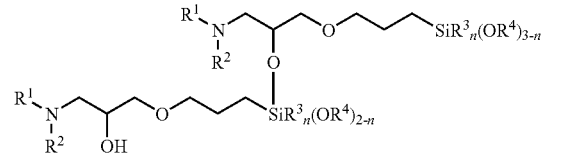

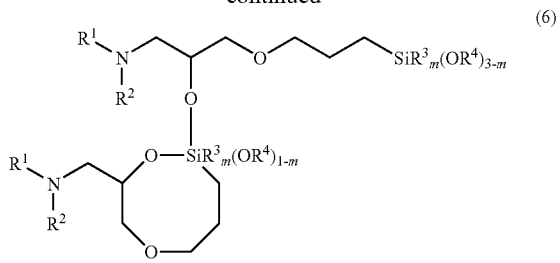

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; n represents an integer of 0 to 2, and m is 0 or 1, with the proviso that m is 0 when n is 0, and m is 1 when n is 1, and compound of the general formula (6) is absent when n is 2 at a weight ratio of 1 to 80%:1 to 70%:1 to 40%:0 to 20%.

5. A method for producing an organosilicon compound having an amino group of claim 1 comprising the steps of reacting an amine compound represented by the following general formula (2):

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; with a γ-glycidoxypropyl alkoxysilane represented by the following general formula (3):

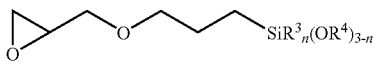

wherein $R^3$ and $R^4$ independently represents an unsubstituted or substituted monovalent hydrocarbon group containing 1 to 10 carbon atoms and n is an integer of 0 to 2; wherein the reaction is conducted while distilling off the alcohol generated in the reaction.

6. A method for producing an organosilicon compound having an amino group according to claim 5 wherein a solvent having a boiling point higher than the alcohol generated in the reaction is used, and the reaction is conducted by refluxing the solvent.

7. A method for producing an organosilicon compound having an amino group according to claim 5 wherein the amine compound represented by the general formula (2) is heated in a distillation tank to a temperature higher than its boiling point for evaporation, and the evaporated amine compound is added to a distillation column from its lower end, while supplying the γ-glycidoxypropylalkoxysilane represented by the general formula (3) to the distillation column from its upper end; and the reaction is conducted while the alcohol generated in the reaction is distilled off from the upper end of the distillation column.

8. A method for producing an organosilicon compound having an amino group according to claim 5 wherein the reaction is conducted in the presence of a basic catalyst.

9. A method for producing an organosilicon compound having an amino group according to claim 5 further comprising the step of distilling the reaction mixture produced by claim 5 in the presence of a basic compound.

10. A method for producing an organosilicon compound having an amino group according to claim 5 wherein the basic compound is an inorganic base.

11. A method for producing an organosilicon compound having an amino group according to claim 5 wherein the basic catalyst is an inorganic base.

12. A method for producing an organosilicon compound having an amino group according to claim 5 wherein the inorganic base is an alkali metal alkoxide.

13. A mixture produced by the method of claim 5 wherein said mixture comprises a compound represented by the following general formula (1), a compound represented by the following general formula (4), a compound represented by the following general formula (5), and a compound represented by the following general formula (6):

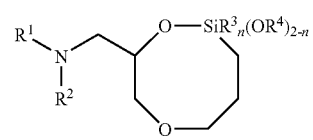

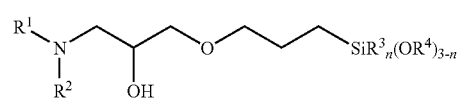

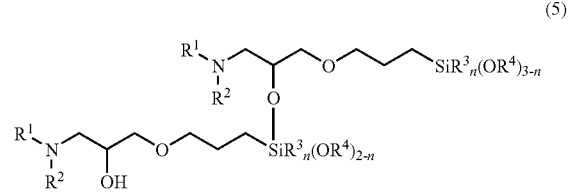

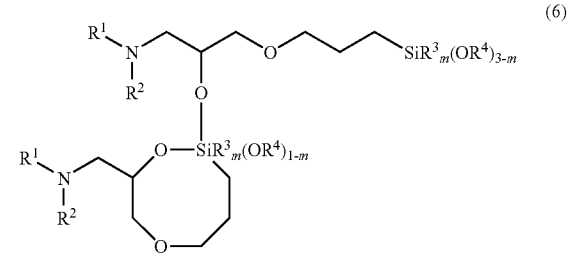

wherein $R^1$ and $R^2$ respectively represent an unsubstituted or substituted aliphatic monovalent hydrocarbon group containing 1 to 10 carbon atoms with the proviso that the $R^1$ and $R^2$ may together form a ring with the nitrogen atom to which they are bonded, and that $R^1$ and $R^2$ may contain a heteroatom; $R^3$ and $R^4$ independently represent an unsubstituted or substituted monovalent hydrocarbon group containing 1 to 10 carbon atoms; n represents an integer of 0 to 2, and m is 0 or 1, with the proviso that m is 0 when n is 0, and m is 1 when n is 1, and compound of the general formula (6) is absent when n is 2 are mixed at a weight ratio of 1 to 90%:0 to 30%:0 to 30%:1 to 60%.

* * * * *